US012559790B2

(12) United States Patent
Daugharthy et al.

(10) Patent No.: US 12,559,790 B2
(45) Date of Patent: Feb. 24, 2026

(54) COMPOSITIONS AND METHODS FOR ANALYTE DETECTION

(71) Applicant: 10x Genomics, Inc., Pleasanton, CA (US)

(72) Inventors: Evan Daugharthy, Cambridge, MA (US); Richard Terry, Carlisle, MA (US); Conor Camplisson, San Marcos, CA (US); David Barclay, Phoenix, AZ (US); Tyler Miselis, Medford, MA (US); Hong Chen, Cambridge, MA (US); Shoshoni Droz, Boston, MA (US)

(73) Assignee: 10X GENOMICS, INC., Pleasanton, CA (US)

( * ) Notice: Subject to any disclaimer, the term of this patent is extended or adjusted under 35 U.S.C. 154(b) by 651 days.

(21) Appl. No.: 17/875,211

(22) Filed: Jul. 27, 2022

(65) Prior Publication Data

US 2023/0212657 A1 Jul. 6, 2023

Related U.S. Application Data

(63) Continuation of application No. PCT/US2021/015578, filed on Jan. 28, 2021.

(60) Provisional application No. 62/967,362, filed on Jan. 29, 2020.

(51) Int. Cl.
*C12Q 1/6841* (2018.01)
*C12Q 1/6869* (2018.01)

(52) U.S. Cl.
CPC ......... *C12Q 1/6841* (2013.01); *C12Q 1/6869* (2013.01)

(58) Field of Classification Search
CPC ............ C12Q 1/6841; C12Q 2523/101; C12Q 2543/101
See application file for complete search history.

(56) References Cited

U.S. PATENT DOCUMENTS

| | | |
|---|---|---|
| 3,501,459 A | 3/1970 | Schindler et al. |
| 3,551,710 A | 12/1970 | Gourdine |
| 3,871,445 A | 3/1975 | Wanka et al. |
| 3,993,233 A | 11/1976 | Bartell |
| 4,123,610 A | 10/1978 | Summerton et al. |
| 4,683,195 A | 7/1987 | Mullis et al. |
| 4,683,202 A | 7/1987 | Mullis |
| 4,800,159 A | 1/1989 | Mullis et al. |
| 4,844,617 A | 7/1989 | Kelderman et al. |
| 4,883,750 A | 11/1989 | Whiteley et al. |
| 4,886,741 A | 12/1989 | Schwartz |
| 4,965,188 A | 10/1990 | Mullis et al. |
| 4,981,985 A | 1/1991 | Kaplan et al. |
| 5,116,742 A | 5/1992 | Cech et al. |
| 5,151,189 A | 9/1992 | Hu et al. |

| | | |
|---|---|---|
| 5,174,670 A | 12/1992 | Takagi et al. |
| 5,210,015 A | 5/1993 | Gelfand et al. |
| 5,244,797 A | 9/1993 | Kotewicz et al. |
| 5,399,491 A | 3/1995 | Kacian et al. |
| 5,424,413 A | 6/1995 | Hogan et al. |
| 5,563,056 A | 10/1996 | Swan et al. |
| 5,594,235 A | 1/1997 | Lee |
| 5,635,352 A | 6/1997 | Urdea et al. |
| 5,684,149 A | 11/1997 | Morrow |
| 5,688,670 A | 11/1997 | Szostak et al. |
| 5,695,940 A | 12/1997 | Drmanac et al. |
| 5,795,236 A | 8/1998 | Alberts et al. |
| 5,830,708 A | 11/1998 | Naughton |
| 5,834,758 A | 11/1998 | Trulson et al. |
| 5,866,337 A | 2/1999 | Schon |
| 5,871,921 A | 2/1999 | Landegren et al. |
| 5,942,391 A | 8/1999 | Zhang et al. |
| 6,063,612 A | 5/2000 | Jayasena et al. |
| 6,068,979 A | 5/2000 | Akhavan-Tafti |
| 6,083,726 A | 7/2000 | Mills, Jr. et al. |
| 6,174,670 B1 | 1/2001 | Wittwer et al. |
| 6,183,960 B1 | 2/2001 | Lizardi |
| 6,183,967 B1 | 2/2001 | Jayasena et al. |
| 6,194,148 B1 | 2/2001 | Hori et al. |
| 6,221,603 B1 | 4/2001 | Mahtani |
| 6,232,067 B1 | 5/2001 | Hunkapiller et al. |
| 6,235,472 B1 | 5/2001 | Landegren et al. |
| 6,287,778 B1 | 9/2001 | Huang et al. |
| 6,287,825 B1 | 9/2001 | Weissman et al. |
| 6,306,597 B1 | 10/2001 | Macevicz |

(Continued)

FOREIGN PATENT DOCUMENTS

| | | |
|---|---|---|
| BR | 112015013784 A2 | 7/2017 |
| BR | 112015013785 A2 | 7/2017 |

(Continued)

OTHER PUBLICATIONS

Kohman et al., "From Designing the Molecules of Life to Designing Life: Future Applications Derived from Advances in DNA Technologies," Angew Chem. Int., vol. 57, pp. 4313-4328. (Year: 2018).*
Lee et al., "Fluorescent in situ sequencing (FISSEQ) of RNA for gene expression profiling in intact cells and tissues," Nature Protocols, vol. 10, No. 3, pp. 442-458. (Year: 2015).*
Bottari et al. Application of FISH technology for microbiological analysis: current state and prospects. Appl Microbiol Biotechnol Dec. 2006; 73(3):485-94.
Donaldson, Julie G. Unit 4.3 Immunofluorescence Staining. Curr Protoc Cell Biol May 2001; 04; Unit 4.3. 9 pages.
Duose, et al. Configuring robust DNA strand displacement reactions for in situ molecular analyses. Nucleic Acids Res. Apr. 2012; 40(7): 3289-3298.

(Continued)

*Primary Examiner* — Young J Kim
(74) *Attorney, Agent, or Firm* — WILSON SONSINI GOODRICH & ROSATI

(57) ABSTRACT

The present disclosure provides methods, systems and compositions for detecting nucleic acid sequences in a biological sample having a three-dimensional matrix. The present disclosure also provides methods, systems and compositions for processing a biological sample for use in nucleic acid sequence detection.

20 Claims, 8 Drawing Sheets

(56) References Cited

U.S. PATENT DOCUMENTS

| | | | |
|---|---|---|---|
| 6,344,239 B1 | 2/2002 | Asai et al. |
| 6,432,360 B1 | 8/2002 | Church |
| 6,485,944 B1 | 11/2002 | Church et al. |
| 6,506,594 B1 | 1/2003 | Barany et al. |
| 6,511,803 B1 | 1/2003 | Church et al. |
| 6,534,266 B1 | 3/2003 | Singer |
| 6,586,176 B1 | 7/2003 | Trnovsky et al. |
| 6,632,655 B1 | 10/2003 | Mehta et al. |
| 6,709,816 B1 | 3/2004 | Huang et al. |
| 6,858,412 B2 | 2/2005 | Willis et al. |
| 6,964,847 B1 | 11/2005 | Englert |
| 7,255,994 B2 | 8/2007 | Lao |
| 7,323,305 B2 | 1/2008 | Leamon et al. |
| 7,427,479 B2 | 9/2008 | Karger et al. |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,745,129 B1 | 6/2010 | Schatz |
| 7,771,949 B2 | 8/2010 | Kramer |
| 7,906,285 B2 | 3/2011 | Drmanac |
| 7,910,304 B2 | 3/2011 | Drmanac |
| 7,941,279 B2 | 5/2011 | Hwang et al. |
| 7,989,166 B2 | 8/2011 | Koch et al. |
| 8,013,134 B2 | 9/2011 | Fredriksson |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,329,404 B2 | 12/2012 | McKernan et al. |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,501,459 B2 | 8/2013 | Chen et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,697,359 B1 | 4/2014 | Zhang |
| 8,871,445 B2 | 10/2014 | Cong et al. |
| 8,906,616 B2 | 12/2014 | Zhang et al. |
| 8,932,814 B2 | 1/2015 | Cong et al. |
| 8,946,389 B2 | 2/2015 | Gao et al. |
| 8,986,926 B2 | 3/2015 | Ferree et al. |
| 8,993,233 B2 | 3/2015 | Zhang et al. |
| 8,999,641 B2 | 4/2015 | Zhang et al. |
| 9,017,992 B2 | 4/2015 | Winther et al. |
| 9,201,063 B2 | 12/2015 | Sood et al. |
| 9,217,151 B2 | 12/2015 | Yin et al. |
| 9,232,067 B2 | 1/2016 | Leigh et al. |
| 9,257,135 B2 | 2/2016 | Ong et al. |
| 9,260,752 B1 | 2/2016 | May et al. |
| 9,267,135 B2 | 2/2016 | Church et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,803,194 B2 | 10/2017 | May et al. |
| 9,896,720 B2 | 2/2018 | Raj et al. |
| 9,909,167 B2 | 3/2018 | Samusik et al. |
| 9,914,967 B2 | 3/2018 | Church et al. |
| 10,030,261 B2 | 7/2018 | Frisen et al. |
| 10,032,064 B2 | 7/2018 | Hoyt |
| 10,036,055 B2 | 7/2018 | Church et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,494,664 B2 | 12/2019 | Doudna et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,538,795 B2 | 1/2020 | Seitz et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisen et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,844,426 B2 | 11/2020 | Daugharthy et al. |
| 10,858,692 B2 | 12/2020 | Church et al. |
| 10,872,679 B2 | 12/2020 | Cai et al. |
| 10,964,001 B2 | 3/2021 | Miller |
| 11,021,737 B2 | 6/2021 | Church et al. |
| 11,021,741 B2 | 6/2021 | Wu et al. |
| 11,078,520 B2 | 8/2021 | Church et al. |
| 11,085,072 B2 | 8/2021 | Church et al. |
| 11,111,521 B2 | 9/2021 | Church et al. |
| 11,118,220 B2 | 9/2021 | Daugharthy et al. |
| 11,193,163 B2 | 12/2021 | Daugharthy et al. |
| 11,293,051 B2 | 4/2022 | Church et al. |
| 11,293,052 B2 | 4/2022 | Church et al. |
| 11,293,054 B2 | 4/2022 | Levner et al. |
| 11,299,767 B2 | 4/2022 | Church et al. |
| 11,312,992 B2 | 4/2022 | Church et al. |
| 11,447,807 B2 | 9/2022 | Church et al. |
| 11,473,139 B2 | 10/2022 | Church et al. |
| 11,542,554 B2 | 1/2023 | Daugharthy et al. |
| 11,549,136 B2 | 1/2023 | Church et al. |
| 11,566,276 B2 | 1/2023 | Church et al. |
| 11,566,277 B2 | 1/2023 | Church et al. |
| 11,639,518 B2 | 5/2023 | Church et al. |
| 11,713,485 B2 | 8/2023 | Daugharthy et al. |
| 11,718,874 B2 | 8/2023 | Daugharthy et al. |
| 2001/0039018 A1 | 11/2001 | Matson et al. |
| 2002/0013003 A1 | 1/2002 | Wagner et al. |
| 2002/0015952 A1 | 2/2002 | Anderson et al. |
| 2002/0029979 A1 | 3/2002 | Freund et al. |
| 2002/0049176 A1 | 4/2002 | Anderson et al. |
| 2002/0117109 A1 | 8/2002 | Hazelton et al. |
| 2002/0127552 A1 | 9/2002 | Church et al. |
| 2002/0155989 A1 | 10/2002 | Efimov et al. |
| 2002/0168645 A1 | 11/2002 | Taylor |
| 2002/0172950 A1 | 11/2002 | Kenny et al. |
| 2002/0182598 A1 | 12/2002 | Zhang |
| 2003/0003490 A1 | 1/2003 | Fan et al. |
| 2003/0018984 A1 | 1/2003 | Coleman et al. |
| 2003/0104459 A1 | 6/2003 | Faham et al. |
| 2003/0148335 A1 | 8/2003 | Shen et al. |
| 2003/0165852 A1 | 9/2003 | Schueler et al. |
| 2003/0228611 A1 | 12/2003 | Chruch et al. |
| 2004/0006035 A1 | 1/2004 | Macejak et al. |
| 2004/0067492 A1 | 4/2004 | Peng et al. |
| 2004/0072014 A1 | 4/2004 | Hasz et al. |
| 2004/0077014 A1 | 4/2004 | Becker |
| 2004/0081962 A1 | 4/2004 | Chen et al. |
| 2004/0081979 A1 | 4/2004 | Knezevic et al. |
| 2004/0086892 A1 | 5/2004 | Crothers et al. |

(56) References Cited

U.S. PATENT DOCUMENTS

| 2004/0126770 A1 | 7/2004 | Kumar et al. |
| 2004/0152072 A1 | 8/2004 | Gerard |
| 2004/0197800 A1 | 10/2004 | Borns |
| 2004/0248144 A1 | 12/2004 | Mir |
| 2004/0259190 A1 | 12/2004 | Naughton |
| 2004/0259226 A1 | 12/2004 | Robey et al. |
| 2005/0032694 A1 | 2/2005 | Sonderegger |
| 2005/0037393 A1 | 2/2005 | Gunderson et al. |
| 2005/0037397 A1 | 2/2005 | Mirkin et al. |
| 2005/0064435 A1 | 3/2005 | Su et al. |
| 2005/0074898 A1 | 4/2005 | Datwani et al. |
| 2005/0106629 A1 | 5/2005 | Mcgrath et al. |
| 2005/0147981 A1 | 7/2005 | Yamakawa et al. |
| 2005/0164207 A1 | 7/2005 | Shapero |
| 2005/0170373 A1 | 8/2005 | Monforte |
| 2005/0176035 A1 | 8/2005 | Crothers |
| 2005/0191687 A1 | 9/2005 | Wang et al. |
| 2005/0221304 A1 | 10/2005 | Xiang et al. |
| 2005/0233318 A1 | 10/2005 | Chee et al. |
| 2006/0019304 A1 | 1/2006 | Hardenbol et al. |
| 2006/0024711 A1 | 2/2006 | Lapidus et al. |
| 2006/0040314 A1 | 2/2006 | Christians et al. |
| 2006/0046311 A1 | 3/2006 | Sun et al. |
| 2006/0077536 A1 | 4/2006 | Bromage et al. |
| 2006/0127916 A1 | 6/2006 | Seul et al. |
| 2006/0177833 A1 | 8/2006 | Brenner |
| 2006/0183107 A1 | 8/2006 | Melkonyan |
| 2006/0216339 A1 | 9/2006 | Ambron et al. |
| 2006/0228733 A1 | 10/2006 | Pierce et al. |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0003949 A1 | 1/2007 | Rava |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0172873 A1 | 7/2007 | Brenner et al. |
| 2007/0190543 A1 | 8/2007 | Livak |
| 2007/0206275 A1 | 9/2007 | Hemmer et al. |
| 2007/0212700 A1 | 9/2007 | Ranganathan et al. |
| 2007/0231823 A1 | 10/2007 | McKernan et al. |
| 2007/0292861 A1 | 12/2007 | Thompson |
| 2007/0292877 A1 | 12/2007 | Dimitrov |
| 2008/0003586 A1 | 1/2008 | Hyde et al. |
| 2008/0003599 A1 | 1/2008 | Dary et al. |
| 2008/0050718 A1 | 2/2008 | Gesteland et al. |
| 2008/0171322 A1 | 7/2008 | Heyduk et al. |
| 2008/0176769 A1 | 7/2008 | Rank et al. |
| 2008/0180790 A1 | 7/2008 | Tafas et al. |
| 2008/0269068 A1 | 10/2008 | Church et al. |
| 2009/0018024 A1 | 1/2009 | Church et al. |
| 2009/0088327 A1 | 4/2009 | Rigatti et al. |
| 2009/0088329 A1 | 4/2009 | Brennan et al. |
| 2009/0093551 A1 | 4/2009 | Bhatia et al. |
| 2009/0099041 A1 | 4/2009 | Church et al. |
| 2009/0105082 A1 | 4/2009 | Chetverin et al. |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2009/0269739 A1 | 10/2009 | Cech et al. |
| 2009/0280559 A1 | 11/2009 | Mccarthy |
| 2009/0325172 A1 | 12/2009 | Milton et al. |
| 2010/0009868 A1 | 1/2010 | Yan et al. |
| 2010/0015607 A1 | 1/2010 | Geiss et al. |
| 2010/0028885 A1 | 2/2010 | Balasubramanian et al. |
| 2010/0049448 A1 | 2/2010 | Doyle et al. |
| 2010/0076057 A1 | 3/2010 | Sontheimer et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0238442 A1 | 9/2010 | Heng et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0090562 A1 | 4/2011 | Brooker |
| 2011/0092376 A1 | 4/2011 | Colston, Jr. et al. |
| 2011/0104693 A1 | 5/2011 | Seligmann |
| 2011/0143955 A1 | 6/2011 | Weiner |
| 2011/0189776 A1 | 8/2011 | Terns et al. |
| 2011/0208040 A1 | 8/2011 | Carmi et al. |
| 2011/0216953 A1 | 9/2011 | Callahan et al. |
| 2011/0223585 A1 | 9/2011 | Gullberg et al. |
| 2011/0223638 A1 | 9/2011 | Wiedenheft et al. |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0065091 A1 | 3/2012 | Willis et al. |
| 2012/0122712 A1 | 5/2012 | Goldstein |
| 2012/0126142 A1 | 5/2012 | Matsui et al. |
| 2012/0252686 A1 | 10/2012 | Umbarger et al. |
| 2012/0270214 A1 | 10/2012 | Bernitz et al. |
| 2012/0277113 A1 | 11/2012 | Huang |
| 2012/0322978 A1 | 12/2012 | Huang |
| 2012/0330636 A1 | 12/2012 | Albou |
| 2013/0017229 A1 | 1/2013 | Mooney et al. |
| 2013/0084574 A1 | 4/2013 | Dong et al. |
| 2013/0130248 A1 | 5/2013 | Haurwitz et al. |
| 2013/0143749 A1 | 6/2013 | Ghadessy et al. |
| 2013/0210031 A1 | 8/2013 | Boyer et al. |
| 2013/0245096 A1 | 9/2013 | Abitbol |
| 2013/0253040 A1 | 9/2013 | Miller et al. |
| 2013/0323729 A1 | 12/2013 | Landegren et al. |
| 2014/0049632 A1 | 2/2014 | Hemmer |
| 2014/0068797 A1 | 3/2014 | Doudna et al. |
| 2014/0087378 A1 | 3/2014 | Chatre et al. |
| 2014/0087427 A1 | 3/2014 | Bujnicki et al. |
| 2014/0179006 A1 | 6/2014 | Zhang |
| 2014/0179770 A1 | 6/2014 | Zhang et al. |
| 2014/0200146 A1 | 7/2014 | Xie et al. |
| 2014/0220578 A1 | 8/2014 | Bohannon et al. |
| 2014/0220587 A1 | 8/2014 | Green, Jr. et al. |
| 2014/0270435 A1 | 9/2014 | Dunn |
| 2014/0273226 A1 | 9/2014 | Wu |
| 2014/0273233 A1 | 9/2014 | Chen et al. |
| 2014/0308695 A1 | 10/2014 | Bruce et al. |
| 2014/0310830 A1 | 10/2014 | Zhang et al. |
| 2014/0315985 A1 | 10/2014 | May et al. |
| 2014/0342457 A1 | 11/2014 | Mali et al. |
| 2014/0364333 A1 | 12/2014 | Wu et al. |
| 2015/0098126 A1 | 4/2015 | Keller et al. |
| 2015/0133319 A1 | 5/2015 | Fu et al. |
| 2015/0247150 A1 | 9/2015 | Zhang et al. |
| 2015/0267251 A1 | 9/2015 | Cai et al. |
| 2016/0002704 A1 | 1/2016 | Diehl et al. |
| 2016/0024524 A1 | 1/2016 | Joung et al. |
| 2016/0106439 A1 | 4/2016 | Menashe |
| 2016/0108458 A1 | 4/2016 | Frei et al. |
| 2016/0153006 A1 | 6/2016 | Zhang et al. |
| 2016/0160210 A1 | 6/2016 | Mali et al. |
| 2016/0265046 A1 | 9/2016 | Zhang et al. |
| 2016/0289740 A1 | 10/2016 | Fu et al. |
| 2016/0304952 A1 | 10/2016 | Boyden et al. |
| 2016/0305856 A1 | 10/2016 | Boyden et al. |
| 2016/0340662 A1 | 11/2016 | Zhang et al. |
| 2016/0355795 A1 | 12/2016 | Ran et al. |
| 2016/0358326 A1 | 12/2016 | Sarachan et al. |
| 2016/0369321 A1 | 12/2016 | Landegren et al. |
| 2016/0376642 A1 | 12/2016 | Landegren et al. |
| 2017/0009278 A1 | 1/2017 | Söderberg et al. |
| 2017/0010672 A1 | 1/2017 | Tanaka et al. |
| 2017/0081489 A1 | 3/2017 | Rodriques et al. |
| 2017/0107566 A1 | 4/2017 | Church et al. |
| 2017/0176338 A1 | 6/2017 | Wu et al. |
| 2017/0191078 A1 | 7/2017 | Zhang et al. |
| 2017/0220733 A1 | 8/2017 | Zhuang et al. |
| 2017/0253918 A1 | 9/2017 | Kohman |
| 2017/0262984 A1 | 9/2017 | Barnes et al. |
| 2018/0010166 A1 | 1/2018 | Pierce et al. |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0282787 A1 | 10/2018 | Walter et al. |

(56) References Cited

U.S. PATENT DOCUMENTS

| | | | |
|---|---|---|---|
| 2019/0017106 A1 | 1/2019 | Frisen et al. |
| 2019/0032128 A1 | 1/2019 | Chen et al. |
| 2019/0085383 A1 | 3/2019 | Church et al. |
| 2019/0119735 A1 | 4/2019 | Deisseroth et al. |
| 2019/0155835 A1 | 5/2019 | Daugharthy et al. |
| 2019/0194709 A1 | 6/2019 | Church et al. |
| 2019/0218608 A1 | 7/2019 | Daugharthy et al. |
| 2019/0241938 A1 | 8/2019 | Levner et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0330617 A1 | 10/2019 | Church et al. |
| 2020/0009786 A1 | 1/2020 | Hikmet et al. |
| 2020/0010891 A1 | 1/2020 | Beechem et al. |
| 2020/0034347 A1 | 1/2020 | Selly |
| 2020/0090786 A1 | 3/2020 | Quiroz Zarate et al. |
| 2020/0140920 A1 | 5/2020 | Pierce et al. |
| 2020/0239946 A1 | 7/2020 | Dewal |
| 2020/0354782 A1 | 11/2020 | Dewal |
| 2021/0017587 A1 | 1/2021 | Cai et al. |
| 2021/0087611 A1 | 3/2021 | Church et al. |
| 2021/0102244 A1 | 4/2021 | Church et al. |
| 2021/0115504 A1 | 4/2021 | Cai et al. |
| 2021/0292834 A1 | 9/2021 | Daugharthy et al. |
| 2021/0310052 A1 | 10/2021 | Daugharthy et al. |
| 2021/0324450 A1 | 10/2021 | Church et al. |
| 2021/0332414 A1 | 10/2021 | Church |
| 2021/0332415 A1 | 10/2021 | Church et al. |
| 2021/0340621 A1 | 11/2021 | Daugharthy et al. |
| 2021/0381049 A1 | 12/2021 | Daugharthy et al. |
| 2022/0016624 A1 | 1/2022 | Daugharthy et al. |
| 2022/0025448 A1 | 1/2022 | Levner et al. |
| 2022/0049303 A1 | 2/2022 | Busby et al. |
| 2022/0145365 A1 | 5/2022 | Church et al. |
| 2022/0228196 A1 | 7/2022 | Church et al. |
| 2022/0251642 A1 | 8/2022 | Church et al. |
| 2022/0282301 A1 | 9/2022 | Levner et al. |
| 2022/0298559 A1 | 9/2022 | Daugharthy et al. |
| 2023/0146821 A1 | 5/2023 | Church et al. |
| 2023/0146985 A1 | 5/2023 | Levner et al. |
| 2023/0212649 A1 | 7/2023 | Church et al. |
| 2023/0212657 A1 | 7/2023 | Daugharthy et al. |
| 2023/0227895 A1 | 7/2023 | Church et al. |
| 2023/0279484 A1 | 9/2023 | Daugharthy et al. |
| 2024/0018569 A1 | 1/2024 | Levner et al. |

FOREIGN PATENT DOCUMENTS

| | | |
|---|---|---|
| BR | 112015008708 A2 | 9/2017 |
| BR | 112015012375 A2 | 9/2017 |
| BR | 112015014425 A2 | 10/2017 |
| BR | 112015022061 A2 | 11/2017 |
| CA | 2891347 A1 | 6/2014 |
| CN | 1432069 A | 7/2003 |
| CN | 1580283 A | 2/2005 |
| CN | 1959384 A | 5/2007 |
| CN | 101285095 A | 10/2008 |
| CN | 101400803 A | 4/2009 |
| CN | 101553306 A | 10/2009 |
| CN | 101608232 A | 12/2009 |
| CN | 101636649 A | 1/2010 |
| CN | 105392898 A | 3/2016 |
| CN | 109923216 A | 6/2019 |
| CN | 109983125 A | 7/2019 |
| EP | 2288726 A2 | 3/2011 |
| EP | 2465943 A2 | 6/2012 |
| EP | 2798092 A2 | 11/2014 |
| EP | 2878671 A1 | 6/2015 |
| EP | 3425063 A1 | 1/2019 |
| EP | 2794928 B1 | 2/2019 |
| EP | 2971184 B1 | 4/2019 |
| EP | 2766498 B1 | 6/2019 |
| EP | 3578666 A1 | 12/2019 |
| EP | 3847274 A1 | 7/2021 |
| EP | 4108782 B1 | 6/2023 |

| | | |
|---|---|---|
| JP | H04268359 A | 9/1992 |
| JP | 2001122892 A | 5/2001 |
| JP | 2007526772 A | 9/2007 |
| JP | 4262799 B2 | 5/2009 |
| JP | 2009538123 A | 11/2009 |
| JP | 2011517555 A | 6/2011 |
| JP | 2012514475 A | 6/2012 |
| JP | 2012518430 A | 8/2012 |
| JP | 2012170337 A | 9/2012 |
| JP | 2014506472 A | 3/2014 |
| JP | 2014513523 A | 6/2014 |
| JP | 2015090458 A | 5/2015 |
| KR | 20080003402 A | 1/2008 |
| WO | WO-9746704 A1 | 12/1997 |
| WO | WO-9856955 A1 | 12/1998 |
| WO | WO-9961665 A2 | 12/1999 |
| WO | WO-0058516 A2 | 10/2000 |
| WO | WO-0126708 A1 | 4/2001 |
| WO | WO-0137266 A1 | 5/2001 |
| WO | WO-0168671 A1 | 9/2001 |
| WO | WO-02057491 A2 | 7/2002 |
| WO | WO-03003810 A2 | 1/2003 |
| WO | WO-03044229 A1 | 5/2003 |
| WO | WO-03102233 A1 | 12/2003 |
| WO | WO-2004104645 A2 | 12/2004 |
| WO | WO-2005082098 A2 | 9/2005 |
| WO | WO-2006138257 A2 | 12/2006 |
| WO | WO-2007001986 A2 | 1/2007 |
| WO | WO-2007076128 A2 | 7/2007 |
| WO | WO-2007086900 A2 | 8/2007 |
| WO | WO-2007121489 A2 | 10/2007 |
| WO | WO-2007123744 A2 | 11/2007 |
| WO | WO-2007149696 A1 | 12/2007 |
| WO | WO-2008041002 A2 | 4/2008 |
| WO | WO-2008069973 A2 | 6/2008 |
| WO | WO-2008108989 A2 | 9/2008 |
| WO | WO-2008157696 A2 | 12/2008 |
| WO | WO-2009046149 A1 | 4/2009 |
| WO | WO-2009046348 A1 | 4/2009 |
| WO | WO-2010054108 A2 | 5/2010 |
| WO | WO-2010080134 A1 | 7/2010 |
| WO | WO-2010087325 A1 | 8/2010 |
| WO | WO-2010104533 A2 | 9/2010 |
| WO | WO-2011092596 A2 | 8/2011 |
| WO | WO-2011143124 A2 | 11/2011 |
| WO | WO-2011143583 A1 | 11/2011 |
| WO | WO-2012005595 A2 | 1/2012 |
| WO | WO-2012019765 A1 | 2/2012 |
| WO | WO-2012058638 A2 | 5/2012 |
| WO | WO-2012083189 A2 | 6/2012 |
| WO | WO-2012110899 A2 | 8/2012 |
| WO | WO-2012129242 A2 | 9/2012 |
| WO | WO-2012150035 A1 | 11/2012 |
| WO | WO-2012164565 A1 | 12/2012 |
| WO | WO-2013055995 A2 | 4/2013 |
| WO | WO-2013096851 A1 | 6/2013 |
| WO | WO-2013098244 A1 | 7/2013 |
| WO | WO-2013119827 A1 | 8/2013 |
| WO | WO-2013126794 A1 | 8/2013 |
| WO | WO-2013141680 A1 | 9/2013 |
| WO | WO-2013142578 A1 | 9/2013 |
| WO | WO-2013176772 A1 | 11/2013 |
| WO | WO-2013184754 A2 | 12/2013 |
| WO | WO-2013188522 A2 | 12/2013 |
| WO | WO-2014022702 A2 | 2/2014 |
| WO | WO-2014048083 A1 | 4/2014 |
| WO | WO-2014065596 A1 | 5/2014 |
| WO | WO-2014089290 A1 | 6/2014 |
| WO | WO-2014093595 A1 | 6/2014 |
| WO | WO-2014093622 A2 | 6/2014 |
| WO | WO-2014093661 A2 | 6/2014 |
| WO | WO-2014093694 A1 | 6/2014 |
| WO | WO-2014099744 A1 | 6/2014 |
| WO | WO-2014113493 A1 | 7/2014 |
| WO | WO-2014144288 A1 | 9/2014 |
| WO | WO-2014150624 A1 | 9/2014 |
| WO | WO-2014163886 A1 | 10/2014 |
| WO | WO-2014182528 A2 | 11/2014 |
| WO | WO-2014191518 A1 | 12/2014 |

(56) References Cited

FOREIGN PATENT DOCUMENTS

| WO | WO-2014197568 A2 | 12/2014 |
| WO | WO-2015002813 A1 | 1/2015 |
| WO | WO-2015116686 A1 | 8/2015 |
| WO | WO-2015118029 A1 | 8/2015 |
| WO | WO-2015127183 A2 | 8/2015 |
| WO | WO-2015148606 A2 | 10/2015 |
| WO | WO-2016007839 A1 | 1/2016 |
| WO | WO-2016028887 A1 | 2/2016 |
| WO | WO-2016081740 A1 | 5/2016 |
| WO | WO-2017015018 A1 | 1/2017 |
| WO | WO-2017019456 A2 | 2/2017 |
| WO | WO-2017027367 A1 | 2/2017 |
| WO | WO-2017079382 A1 | 5/2017 |
| WO | WO-2017079406 A1 | 5/2017 |
| WO | WO-2017143155 A2 | 8/2017 |
| WO | WO-2017161251 A1 | 9/2017 |
| WO | WO-2017189525 A1 | 11/2017 |
| WO | WO-2018045181 A1 | 3/2018 |
| WO | WO-2018045186 A1 | 3/2018 |
| WO | WO-2018089445 A1 | 5/2018 |
| WO | WO-2018187791 A1 | 10/2018 |
| WO | WO-2019103996 A1 | 5/2019 |
| WO | WO-2019217758 A1 | 11/2019 |
| WO | WO-2020028194 A1 | 2/2020 |
| WO | WO-2020076976 | 4/2020 |
| WO | WO-2020076979 A1 | 4/2020 |
| WO | WO-2020096687 A1 | 5/2020 |
| WO | WO-2020198071 A1 | 10/2020 |
| WO | WO-2021155063 | 8/2021 |
| WO | WO-2021168326 | 8/2021 |

OTHER PUBLICATIONS

Duose et al. Supporting Information to: Configuring robust DNA strand displacement reactions for in situ molecular analyses. 2012. 5 pages.

Duose et al. Supporting Information to: Multiplexed and Reiterative Fluorescence Labeling via DNA Circuitry. Bioconjugate Chem 2010. 4 pages.

Feature Analysis of Claim 1 from Opposition to European Patent No. EP4108782B1 filed by NanoString Technologies Inc., dated Jul. 18, 2023. 1 page.

Goransson et al. Supplementary Data to: A Single Molecule Array for Digital Targeted Molecular Analyses. Nucleic Acids Research, vol. 37, Issue 1, 2009. 5 pages.

Gunderson, et al. Decoding Randomly Ordered DNA Arrays. Genome Res. 14(5):870-877, 2004.

Henegariu et al. Colour-changing karyotyping: an alternative to M-FISH/SKY. Nature Genetics 23, 263-264 (1999).

Huang et al., Super-resolution fluorescence microscopy, Annu Rev Biochem. 2009;78: 993-1016, First published: Apr. 2, 2009.

"Hybridisation". Extract from Oxford Dictionary of Biochemistry and Molecular Biology, Second Edition, 2006. 4 pages.

Olejnik et al. Photocleavable aminotag phosphoramidites for 5'-termini DNA/RNA labeling. Nucleic Acids Research, 1998, vol. 26, No. 15, 3572-3576.

Opposition to European Patent No. EP4108782B1 filed by NanoString Technologies Inc., dated Jul. 18, 2023. 83 pages.

"Probe". Extract from Oxford Dictionary of Biochemistry and Molecular Biology, Second Edition, 2006. 4 pages.

Schubert et al. Analyzing proteome topology and function by automated multidimensional fluorescence microscopy. Nature Biotechnology, 2006. 9 pages.

Soderberg, O. et al., "Characterizing proteins and their interactions in cells and tissues using the in situ proximity ligation assay," Methods, 2008;45(3):227-32.

Stryer et al. Biochemistry, Fifth Edition. pp. 124-125. 2002.

U.S. Appl. No. 61/579,265, inventors Levner; Daniel et al., filed Dec. 22, 2011.

Veccham et al. A Non-perturbative pairwise-additive analysis of charge transfer contributions to intermolecular interaction energies. Physical Chemistry Chemical Physics, 2020. 48 pages.

Zhen, et al. Poly-FISH: a technique of repeated hybridizations that improves cytogenetic analysis of fetal cells in maternal blood. Prenat Diagn. 1998; 18(11):1181-5.

Nakano et al. Effects of Molecular Crowding on the Structures, Interactions, and Functions of Nucleic Acids. Chem. Rev. 2014, 114, 5, 2733-2758.

Abramoff, Michael, et al. Image Processing with ImageJ. Biophotonics International. vol. 11, Issue No. 7 (2003): 36-42.

Bioptechs, FCS2 (Focht Live-Cell Chamber System) Instructions (2007): 1-6. Retrieved on URL: http://www.bioptechs.com/Instructions/FCS2_i/fcs2-3_i.htm.

Brileya, Kristen, et al. Biofilm Growth Mode Promotes Maximum Carrying Capacity and Community Stability During Product Inhibition Syntrophy. Frontiers in Microbiology. vol. 5, Article No. 693 (2014): 1-14.

Bui, Duy, et al. Analytical Devices Based on Light-emitting Diodes—a Review of the State-of-the-art. Analytica Chimica Acta. vol. 853 (2015): 46-58.

Chirieleison, Steven, et al. Automated Live Cell Imaging Systems Reveal Dynamic Cell Behavior. Biotechnology Progress. vol. 27, Issue No. 4 (2011): 913-924.

Delaune, Emilie, et al. Single-cell-resolution Imaging of the Impact of Notch Signaling and Mitosis on Segmentation Clock Dynamics. Developmental Cell. vol. 23, Issue No. 5 (2012): 995-1005.

Ehrlicher, Allen, et al. Optical Neuronal Guidance. Methods in Cell Biology. vol. 83 (2007): 495-520.

Fang-Yen, Christopher, et al. Video-rate Tomographic Phase Microscopy. Journal of Biomedical Optics. vol.16, Issue No. 1 (2011): 011005-1-011005-5.

Femino, Andrea M, et al. Visualization of Single Molecules of mRNA in Situ. Methods in Enzymology. vol. 361 (2003): 245-304.

Fischer, Robert, et al. Microscopy in 3D: a Biologist's Toolbox. Trends in Cell Biology. vol. 21, Issue No. 12 (2011): 682-691.

FluoSpheres™ Carboxylate-Modified Microspheres. Thermo Fischer Scientific. Retrieved from: https://www.thermofisher.com/order/catalog/product/F8809. (2024).

Gerhardt, Ilja, et al. Detection of Single Molecules Illuminated by a Light-emitting Diode. Sensors. vol. 11, Issue No. 1 (2011): 905-916.

Hamilton, HVXM 8-5 Valve Laboratory Products. Retrieved from URL on Mar. 7, 2024: https://www.hamiltoncompany.com/laboratoryproducts/valves/36766.

Harvard Apparatus, PHD 22/2000 Syringe Pump Series User's Manual, (1996).

Hattori, Akifumi , et al. Single-molecule Imaging With an Inexpensive UV-LED Light Source. Chemistry Letters. vol. 38, Issue No. 3 (2009): 234-235.

Hodneland, Erlend, et al. CellSegm—a MATLAB Toolbox for High-throughput 3D Cell Segmentation. Source Code for Biology and Medicine. vol. 8, Issue No. 16 (2013): 1-24.

James, Paul, Water Objectives a Personal Exploration . . . all is Not What It Seems. Microscopy UK 1-8 (2004). Retrieved from URL: http://www.microscopy-uk.org.uk/mag/indexmag.html?http://www.microscopy-uk.org.uk/mag/artoct04/pjwater.html.

Kuo, Jason, et al. High-power Blue/UV Light-emitting Diodes as Excitation Sources for Sensitive Detection. vol. 25, Issue No. 21-22 (2004): 3796-3804.

Moffit, et al. RNA Imaging With Multiplexed Error-Robust. Methods in Enzymology. vol. 572 (2016): 1-49.

Nikon MicroscopyU, Culture Chambers for Live-Cell Imaging, Retrieved from: https://web.archive.org/web/20150810165805/http://www.microscopyu.com:80/articles/livecellim aging/culturechambers.html. (2015).

Niman, Cassandra, et al. Controlled Microfluidic Switching in Arbitrary Time-sequences With Low Drag. Lab on a Chip. vol. 13 (2013): 2389-2396.

North, Alison J, Seeing is Believing? A Beginners' Guide to Practical Pitfalls in Image Acquisition. The Journal of Cell Biology. vol. 172, Issue No. 1 (2006) :9-18.

(56) References Cited

OTHER PUBLICATIONS

O'Connor, Clare, Fluorescence In Situ Hybridization (FISH). Nature Education. vol. 1, Issue No. 1 (2008). Retrieved from URL: https://www.nature.com/scitable/topicpage/fluorescence-in-situ-hybridization-fish-327.

Olympus Lifescience, Instructions IX71/IX51 Inverted Research Microscope/Inverted Basic Microscope, (2005) at https://www.ucc.ie/en/media/academic/anatomy/imagingcentre/icdocuments/OLYMPUSIX71_manual.pdf.

Olympus Lifescience, Inverted Research System Microscopes IX71/IX81 IX2 Series Manual Olympus IX-71 (2009). Retrieved from: https://afns-labs.ualberta.ca/wp-content/uploads/sites/58/2018/05/Olympus-IX81-brochure.pdf.pdf.

Olympus Lifescience. Research Inverted System Microscope IX71/IX81 IX2 Series (2005), Retrieved from: https://www.olympus-lifescience.com/data/olympusmicro/brochures/pdfs/ix71.pdf?rev=EABE.

Pedersen, Peder Skafte, et al. A Self-contained, Programmable Microfluidic Cell Culture System With Real-time Microscopy Access. Biomedical Microdevices. vol. 14, Issue No. 2 (2012): 385-399.

Perillo, Evan P, et al. Enhanced 3D Localization of Individual RNA Transcripts via Astigmatic Imaging (2014). SPIE Conference Proceedings. vol. 8950 (2014): 895003-1 895003-11.

Querido, Emmanuelle, et al. Using Fluorescent Proteins to Study mRNA Trafficking in Living Cells. Methods in Cell Biology. Vol.85 (2008): 273-292.

Richard, Marc J P, et al. Cellular Mechanisms by Which Lipoic Acid Confers Protection During the Early Stages of Cerebral Ischemia: a Possible Role for Calcium. Neuroscience Research. vol. 69, Issue No. 4 (2011): 299-307.

Sands, Gregory, et al. Automated Imaging of Extended Tissue Volumes Using Confocal Microscopy. Microscopy Research and Technique. vol. 67, Issue No. 5 (2005): 227-239.

Schneider, Caroline, et al. NIH Image to ImageJ: 25 Years of Image Analysis. Nature Methods. Vol. 9, Issue No. 7 (2012): 671-675.

Shah, Sheel, et al. Dynamics and Spatial Genomics of the Nascent Transcriptome by Intron seqFISH. Cell. vol. 174, Issue No. 2 (2018): 363-376.

Shen, Feimo, et al. 32 Digital Autofocus Methods for Automated Microscopy. Methods in Enzymology. vol. 414 (2006): 620-632.

Sivaramakrishnan, Sivaraj, et al. Shear Stress Induced Reorganization of the Keratin Intermediate Filament Network Requires Phosphorylation by Protein Kinase C Zeta. Molecular biology of the cell. vol. 20, Issue No. 11 (2009): 2755-2765.

Spector, David L, et al. [75] Observation of Live Cells in the Light Microscope. Cells a Laboratory Manual. vol. 2 (1998):75.1-75.13.

Thermo Fischer Scientific, Fluorescence SpectraViewer, Retrieved on Feb. 29, 2024, from: https://www.thermofisher.com/order/fluorescence-spectraviewer/#!/.

Tirichine, Leïla, et al. 3D Fluorescent in Situ Hybridization Using Arabidopsis Leaf Cryosections and Isolated Nuclei. Plant Methods. vol. 5, Article 11 (2009): 1-7.

Toomre, Derek, et al. A New Wave of Cellular Imaging. Annual Review of Cell and Developmental Biology. vol. 26 (2010): 285-287.

U.S. Pat. No. 11,542,554—*Nanostring Technologies, Inc.* (Petitioner) v. *President and Fellows of Harvard College.* Petition for Inter Partes Review dated Jan. 30, 2024.

U.S. Appl. No. 17/395,534 Notice of Allowance dated Jun. 21, 2022.

U.S. Appl. No. 17/395,534 Office Action dated Mar. 4, 2022.

Wessels, Johannes, et al. Light-emitting Diodes in Modern Microscopy—from David to Goliath ?. Cytometry. vol. 81, Issue No. 3 (2012): 188-197.

Winer, Michael, et al. Application of a Three-dimensional (3D) Particle Tracking Method to Microfluidic Particle Focusing. Lab on a Chip. vol. 14 (2014): 1443-1451.

Xiao, Jie, Single-Molecule Imaging in Live Cells. Handbook of Single-Molecule Biophysics (2009): 43-93.

Zessin, Patrick, et al. A Hydrophilic Gel Matrix for Single-molecule Super-resolution Microscopy. Optical Nanoscopy. vol. 2, Issue No. 4 (2013): 1-8.

Bálint, et al. Correlative live-cell and superresolution microscopy reveals cargo transport dynamics at microtubule intersections. Proceedings of the National Academy of Sciences. Feb. 2, 20136;110(9): pp. 3375-3380.

Baner et al. Parallel gene analysis with allele-specific padlock probes and tag microarrays. Nucleic Acids Research. 2003;31(17):e103.

Baner, et al. Signal amplification of padlock probes by rolling circle replication. Nucleic Acids Res. Nov. 15, 1998;26(22):5073-8.

Chen et al. "Spatially resolved, highly multiplexed RNA profiling in single cells". Science. Apr. 24, 2015;348(6233):aaa6090.

Leone, et al. Molecular beacon probes combined with amplification by NASBA enable homogeneous, real-time detection of RNA. Nucleic Acids Res. May 1, 1998;26(9):2150-5.

Manders, et al. Direct imaging of DNA in living cells reveals the dynamics of chromosome formation. The Journal of cell biology. Mar. 8, 1999;144(5):813-821.

Tam et al. A Microfluidic Platform for Correlative Live-Cell and Super-Resolution Microscopy. PLoS One. Dec. 2, 20149;9(12):e115512.

Tian et al.: Accurate multiplex gene synthesis from programmable DNA microchips. Nature. 432(7020):1050-1054 (2004).

Wang, et al. Allele quantification using molecular inversion probes (MIP). Nucleic Acids Research. 2005; 33(21); e183 (14 pages).

Choi, Harry M T. et al. Supplemental Information: Programmable In Situ Amplification for Multiplexed Bioimaging. Nature Biotechnology 28(11): 1208-1212 (2010).

Islam, Saiful, et al., Characterization of the single-cell Transcriptional landscape by Highly Multiplex RNA-seq. Genome Research 21(7):1160-1167 (2011).

Larsson et al. In situ genotyping individual DNA molecules by target-primed rolling-circle amplification of padlock probes. Nat Methods1:227-232 (2004).

Lee, Je Hyuk et al. Supplemental Information: Highly multiplexed subcellular RNA sequencing in situ. Science 343(6177):1360-1363 (2014).

"LSM 710 and ConfoCor 3 Operating Manual," Carl Zeiss Microlmaging GmbH, pp. 7-13, 44-47, 73-74, 77-81, (Apr. 2009).

Mali, P. et al., "Supplementary Materials for RNA-Guided Human Genome Engineering via Cas9," SCIENCE, vol. 339, No. 6121, Jan. 3, 2013 (Jan. 3, 2013), pp. 1-36.

"TCS-SP5 Ver2.0 Manual," Leica Microsystems, Inc., pp. 1-11, 15, 24-26, 153 (Feb. 21, 2011).

Weibrecht, Irene et al. In situ detection of individual mRNA molecules and protein complexes or post-translational modifications using padlock probes combined with the in situ proximity ligation assay. Nature protocols 8(2): 355-372 (2013).

Zenklusen, Daniel and Singer, Robert H. "Analyzing mRNA Expression Using Single mRNA Resolution Fluorescent in Situ Hybridization" Methods in Enzymology, vol. 470, https://www.ncbi.nlm.nih.gov/pmc/articles/PMC3162037/, pp. 1-17, Mar. 1, 2010.

AbouHaidar, et al., Non-enzymatic RNA Hydrolysis promoted by the combined catalytic activity of buffers and magnesium Ions. Verlag der Zeitschrift fur naturforschung. Tubingen. 1999; 54c: 542-548.

Achim et al., High-throughput spatial mapping of single-cell RNA-seq data to tissue of origin. Nature Biotechnology, vol. 33, No. 5, May 2015, p. 503-511.

A.D. Bates et al., "DNA gyrase can supercoil DNA circles as small as 174 base pairs," The EMBO Journal, vol. 8, No. 6 pp. 1861-1866, 1989.

Agaoglu et al. Ultra-sensitive microfluidic wearable strain sensor for intraocular pressure monitoring. Lab on a Chip, Issue 22, 2018; pp. 3471-3483.

Al-Attar et al., Clustered Regularly Interspaced Short Palindromic Repeats (CRISPRs ): The Hallmark of an Ingenious Antiviral Defense Mechanism in Prokaryotes, Bio Chem. (2011) vol. 392, Issue 4, pp. 277-289.

Alberti Elena et al: "Covalent and non-covalent binding of metal complexes to RNA",Journal of Inorganic Biochemistry, Elsevier

(56) References Cited

OTHER PUBLICATIONS

Inc, US, vol. 163, Jun. 8, 2016 (Jun. 8, 2016), pp. 278-291, XP029790866, ISSN: 0162-0134, DOI:10.1016/J.JINORGBIO.2016. 04.021.

Altshuler D, Daly MJ, Lander ES. 2008. "Genetic mapping in human disease" Science 322: 881-8.

Amasino et al., Acceleration of nucleic acid hybridization rate by polyethylene glycol, Analytical biochemistry, vol. 152, No. 2, Feb. 1, 1986.

Ann-Christine Syvanen, "Toward genome-wide SNP genotyping," Nature Genetics Supplement, vol. 37, Jun. 2005, pp. S5-S10.

Ansari et al, Rioboactivators: Transcription activation by non-coding RNA, Grit Rev Biochem Mol Bioi. 2009 ; 44(1 ): 50-61.

Arezi et al., Novel mutations in Moloney Murine Leukemia Virus reverse transcriptase increase thermostability through tighter binding to template-primer. Nucleic Acids Research 37(2) : 473-481 (Year: 2009).

Ascano., Identification of RNA-protein interaction networks using PAR-CLIP. Wiley interdisciplinary reviews. RNA 3.2 (Mar. 2012): 159-177, DOI:10.1002/wma.1103.

Bakal C, Aach J, Church G, Perrimon N. 2007. "Quantitative morphological signatures define local signaling networks regulating cell morphology" Science 316: 1753-6.

Ball et al. Targeted and genome-scale methylomics reveals gene body signatures in human cell lines. Nat. Biotechnol 27:361-368 (2009).

Bang D, Church GM. 2008. "Gene synthesis by circular assembly amplification" Nat Methods 5: 37-9.

Bao, et al. A Novel DNA Detection Method Based on Gold Nanoparticle Probes and Gene Chips. Acta Chimica Sinica No. 18, 2144-2148. 2009. English Abstract provided.

Beliveau, Brian J. et al., Versatile design and synthesis platform for visualizing genomes with Oligopaint FISH probes, National Academy of Sciences, vol. 109, No. 52, Dec. 11, 2012, pp. 21301-21306.

Beliveau, Brian J. et al., Visualizing Genomes with Oligopaint Fish Probes: In: "Current Protocols in Molecular Biology", Jan. 6, 2014, Wiley, New York, NY.

Beliveau, et al. Single-molecule super-resolution imaging of chromosomes and in situ haplotype visualization using olligopaint FISH probes. Nat Commun. 2015; 6:7147; Abstract, p. 3 [according to the posted document], Fig 1 and its legend; p. 4, Fig 2 and its legend; p. 6, Fig 3 and its legend.

Bell J. 2004. "Predicting disease using genomics" Nature 429: 453-6.

Bibikova et al. "Quantitative Gene Expression Profiling in Formalin-Fixed, Paraffin-Embedded Tissues Using Universal Bead Arrays" American Journal of Pathology, vol. 165, No. 5, Nov. 2004.

Bock, RM. Alkaline Hydrolysis of RNA. Methods in Enzymology 12 : 224-228 (Year: 1967).

Bouche et al., The effect of spermidine on endonuclease inhibition by agarose contaminants. Analytical biochemistry, Academic press, vol. 115, No. 1, Jul. 15, 1918, pp. 42-45.

Brenner, et al., Gene Expression analysis by massively parallel signature sequencing (MPSS) on microbead arrays. Nature Biotechnology 18.6 (Jun. 2000): 630-634, doi:10.1038/76469.

Brenner, et al. "In vitro cloning of complex mixtures of DNA on microbeads: physical separation of differentially expressed cDNAs." Proc Natl Acad Sci U S A. Feb. 15, 2000;97(4):1665-70.

Brown et al., Review Article : In situ Hybridization with Riboprobes :An Overview for Veterinary Pathologists. Veterinary Pathology 35 : 159-167 (Year: 1998).

C.A Hutchison III et al., "Cell-free cloning using 029 DNA polymerase," 17332-17336, PNAS, Nov. 29, 2005, vol. 102, No. 48.

Cao, et al., In-situ Immuno-PCR to detect antigens. The Lancet 356 (Sep. 2000): 1002-1003.

Capodieci et al. "Gene expression profiling in single cells within tissue" Nature Methods, Sep. 14, 2005, 2(9) pp. 663-665.

Carroll, "A CRISPR Approach to Gene Targeting" 20(9) Molecular Therapy 1658-1660 (Sep. 2012).

Chen, Baohui et al. Dynamic Imaging of Genomic Loci in Living Human Cells by an Optimized CRISPR/Cas System. Cell. vol. 155, No. 7. (2013): 1479-1491.

Chen, et al., Expansion Microscopy. Science, Jan. 30, 2015; vol. 347, Issue 6221: 543-549.

Chen et al., Functional organization of the human 4D Nucleome, PNAS Jun. 30, 2015 112 (26) 8002-8007; first published Jun. 15, 2015.

Chen, et al., Nanoscale imaging of RNA with expansion microscopy. Nature Methods. Aug. 2016; vol. 13, No. 8: pp. 679-687.

Chen, Kai et al., Expansion microscopy imaging technique and its application, Chinese journal of analytical chemistry, vol. 47, No. 5, May 1, 2019. pp. 643-651.

Cheng, et al. Multiplexed Activation of Endogenous Genes by CRISPR-on, An RNA-Guided Transcriptional Activator System. Cell Research. vol. 23. No. 10. Oct. 1, 2013. pp. 1163-1171.

Chiang DY, Getz G, Jaffe DB, O'Kelly MJ, Zhao X, Carter SL, Russ C, Nusbaum C, Meyerson M, Lander ES. 2009. High-resolution mapping of copy-number alterations with massively parallel sequencing Nat Methods 6: 99-103. Pmc Id: PMC2630795.

Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).

Choi et ai. Programmable in situ amplification for multiplexed imaging of mRNA expression. Nature Biotechnology 28(11): 1208 (Year: 2010).

Choi, et al., Next-Generation in Situ Hybridization Chain Reaction: Higher Gain, Lower Cost, Greater Durability. ACS NANO 8.5 (May 2014): 4284-4294, XP055409053, US.

Choy et al. 2008. "Genetic analysis of human traits in vitro: drug response and gene expression in lymphoblasloid cell lines" PLoS Genet 4: e1000287. PMC ID: PMC2583954.

Chozinski, et al., Expansion microscopy with conventional antibodies and fluorescent proteins. Nature Methods. Jun. 2016; vol. 13, No. 6: pp. 485-491.

Christian et al. 2001. "Detection of DNA point mutations and mRNA expression levels by rolling circle amplification in individual cells" Proc Nall Acad Sci U SA 98: 14238-43. PMC ID: PMC64666.

Church et al. 2008. "High-Speed Imaging for DNA Sequencing" Biopholonics ( http://NWW.pholonics.com/Conlenl/ReadArticle. aspx? ArticleID=33989).

Church et al.; Center for Casual Consequences of Variation {CCV) "An NHGRI Center for Excellence in Genomic Science" http://ccv. med.harvard.edu; Wayback Machine {Jul. 3, 2011).

Church et al.; Center for Casual Consequences of Variation {CCV) "Our four Specific Aims" http://ccv.med.harvard. edu/specific_aims. htm; Wayback Machine {Aug. 13, 2011).

Church GM. 2006. "Genomes for all" Sci Am 294: 46-54.

Church; "Proposal for a Center for the determination of the Causal Transcriptional Consequences of Human Genetic Variation (CTCHGV)" http://ccv.med.harvard.edu/CEGS09_Complete_Proposal_minus_Admin_Sections.09May21.final.pdf; Wayback Machine (Aug. 13, 2011).

Clausson et al., Compaction of rolling circle amplification products increases signal integrity and signal-to-noise ratio. Scientific Reports, vol. 5. Jul. 23, 2015. p. 12317.

Codeluppi, et al., Spatial organization of the somatosensory cortex revealed by osmFISH. Nature Methods, Nov. 2018; vol. 15: 932-935.

Cong et al.: Multiplex genome engineering using CRISPR/Cas systems. Science 339(6121):819-823 (2013).

Conze et al. "Single molecule analysis of combinatorial splicing" Nucleic Acids Research, Jun. 29, 2010, vol. 38, No. 16; e163.

Cookson W, Liang L, Abecasis G, Moffatt M, Lathrop M. 2009. "Mapping complex disease traits with global gene expression" Nat Rev Genet 10: 184-94.

CRISPR in the Lab: A Practical Guide [online]. Addgene. Sep. 4, 2014. Retrieved on Dec. 4, 2014. Retrieved from the Internet: URL: https://www.addgene.org/CRISPR/guide/.

(56) References Cited

OTHER PUBLICATIONS

Dahl, et al. Circle-to-circle amplification for precise and sensitive DNA analysis. Proc Natl Acad Sci U S A. Mar. 30, 2004;101(13):4548-53. Epub Mar. 15, 2004.

Dasari, et al., Platform for Spatial Molecular Data by Vivek Dasari 1-7 Signature redacted Thesis Supervisor. (Aug. 2015) XP055559164, URL: http://dspace.mit.edu/bitstream/handle/1721.1/107103/971494098-MIT.pdf?sequence=1.

Davies et al. Crystal Structure of the ribonuclease H domain of HIV-1 Reverse Transcriptase. Science 252 :88 (Year: 1991).

De Bakker PI, Yelensky R, Pe'er I, Gabriel SB, Daly MJ, Altshuler D. 2005. "Efficiency and power in genetic associalior studies" Nat Genet 37: 1217-23.

Deng et al., Targeted bisulfite sequencing reveals changes in DNA methylation associated with nuclear reprogramming. Nat Biotechnol. 27 (4):353-360 (2009).

Dicarlo, et al. Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.

Dirks et al., Triggered amplification by hybridization chain reaction, PNAS 101(43) : 15275 (Year: 2004).

Dixon et al. 2007. "A genome-wide association study of global gene expression" Nat Genet 39:1202-7.

Doillon, et al., Actin Filaments in Normal Dermis and During Wound Healing. The American Journal of Pathology 126.1 (1987): 164-170.

Duose, et al. Multiplexed and Reiterative Fluorescence Labeling via DNA Circuitry. Bioconjug Chem. Dec. 15, 2010; 21(12): 2327-2331.

Eberwine et al. 2001. "mRna expression analysis of tissue sections and single cells" J Neurosci 21: 8310-4.

Eid et al. 2009. "Real-time DNA sequencing from single polymerase molecules" Science 323: 133-8.

Eliscovich, et al., mRNA on the move: The road to its biological destiny. Journal of Biological Chemistry 288.28 (Jul. 2013): 20361-20368.

Emilsson et al. 2008; "Genetics of gene expression and its effect on disease" Nature 452: 423-8.

Femino et al. "Visualization of Single RNA Transcripts in Situ" Science, Apr. 24, 1998, vol. 280, pp. 585-590.

Fu et al. Improving CRISPR-Cas nuclease specificity using truncated guide RNAs. Nat Biotechnol 32(3):279-284 (2013).

Gao, et al., An Efficient strategy for sequencing-by-synthesis. Journal of Nanoscience and nanotechnology. 2010; 10:2988-2993.

Gasiunas et al. Cas9-crRNA ribonucleoprotein complex mediates specific DNA cleavage for adaptive immunity in bacteria. PNAS USA 109:E2579-E2586 (2012).

Gavrilovic et al. "Automated Classification of Multicolored Rolling Circle Products in Dual-Channel Wide-Field Fluorescence Microscopy" Cytometry Part A, Jul. 2011, 79(7), pp. 518-527.

Geiss, et al. Direct multiplexed measurement of gene expression with color-coded probe pairs. Nat Biotechnol. Mar. 2008;26(3):317-25. doi: 10.1038/nbt1385. Epub Feb. 17, 2008.

Gilbert et al., CRISPR-Mediated modular RNA-guided regulation of transcription in Eukaryotes. Cell 154(2): 442-451 (2013).

Ginart, et al., RNA Sequencing In Situ. Nat Biotechnol 32.6 (Jun. 2014): 543-544, DOI:10.1038/nbt.2921.

Gohring et al., The Scaffold/Matrix Attachment Region Binding Protein hnRNP-U (SAF-A) Is Directly Bound to Chromosomal DNA in Vivo: A Chemical Cross-Linking Study†. Biochem., 1997: vol. 36, pp. 8276-8283.

Goransson et al.: A single molecule array for digital targeted molecular analyses. Nucleic Acids Res. 37(1):e7:1-9 doi: 10.1093/nar/gkn921 (2009).

Grompe, The rapid detection of unknown mutations in nucleic acids. Nature Genetics (Oct. 1993): 111-117, DOI: 10.1038/ng1093-111.

Gu et al. "Multiplex single-molecule interaction profiling of DNA-barcoded proteins," Nature, Sep. 21, 2014 (Sep. 21, 2014), vol. 515, pp. 54-557 and Supplementary Information. entire document.

Gunderson et al., Decoding randomly ordered DNA arrays. Genome Research. 14(5):870-877 (2004).

Guo et al. "Target-driven DNA association to initiate cyclic assembly of hairpins for biosensing and logic gate operation" Chemical Science, 2015, 6, pp. 4318-4323.

Gusev, et al., Rolling circle amplification: a new approach to increase sensitivity for immunohistochemistry and flow cytometry. Am J Pathol . Jul. 2001;159(1):63-9. doi: 10.1016/S0002-9440(10)61674-4.

H. Yan et al., "Allelic Variation in Human Gene Expression," Science, vol. 297, Aug. 16, 2002, p. 1143, www. sciencemag.org.

Hale et al., Essential Features and Rational Design of CRISPR RNAs That Function With the Cas RAMP Module Complex to Cleave RNAs, Molecular Cell, (20 12) vol. 45, Issue 3, 292-302.

Han, et al., Quantum-dot-tagged microbeads for multiplexed optical coding of biomolecules. Nature Biotechnology 19.99 (Jul. 2001): 631-635.

Hansen et al., Sensitive ligand-based protein quantification using immuno-PCR: A critical review of single-probe and proximity ligation assays. Biotechniques 56:217-228 (Year: 2014).

Harris et al. 2008. "Single-molecule DNA sequencing of a viral genome" Science 320: 106-9.

Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.

Hirsch et al. (2002) "Easily reversible desthiobiotin binding to streptavidin, avidin, and other biotin-binding proteins: uses for protein labeling, detection, and isolation." Analytical of Biochemistry 308(2):343-357.

Ho et al. "Sequencing by ligation variation with endonuclease V digestion and deoxyinosine-containing query oligonucleotides" BMC Genomics, 2011, 12:598.

International HapMap C. 2005. "A haplotype map of the human genome" Nature 437: 1299-1320. PMCID: PMC1880871.

Itzkovitz et al. "Single molecule transcript counting of stem cell markers in the mouse intestine" Nat Cell Biol., Nov. 2011, 14(1), pp. 106-114.

Itzkovitz et al., Validating transcripts with probes and imaging technology. Nat Methods. 8(4 Suppl):S12-9 (2011).

J. B. Fan et al., "Parallel Genotyping of Human SNPs Using Generic High-density Oligonucleotide Tag Arrays," 3enome Research, 2000, 10:853-860.

J. Baner et al., "Signal amplification of padlock probes by rolling circle replication," Nucleic Acids Research, 1998, vol. 26, No. 22, pp. 5073-5078.

J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.

J. M. Shumaker et al., "Mutation Detection by Solid Phase Primer Extension," Human Mutation 7:346-354 (1996).

J. Tian et al., "Accurate multiplex gene synthesis from programmable DNA microchips," Nature, vol. 432, Dec. 23-30, 2004, pp. 1050-1054, www.nature.com/nature.

Jambhekar, et al., Cis-acting Determinants of Asymmetric, Cytoplasmic RNA Transport. RNA 13 (2007): 625-642.

Jarvius et al. Digital quantification using amplified single-molecule detection. Nat Methods 3:725-727 (2006).

Jiang et al. "Solar thermal polymerase chain reaction for smartphone-assisted molecular diagnostics" Scientific Reports, 4:4137, 2014.

Jinek , et al. 'RNA-programmed genome editing in human cells.' eLite 2013;2:e00471 . [retrieved 1-3, 6, 7, 10-12 on Jun. 3, 2014). Retrieved rom the Internet. URL: http://elife.elifesciences.org/content/2/e00471 . entire document.

Jinek et al. A programmable dual-RNA-guided DNA endonuclease in adaptive bacterial immunity. Science 337(6096):816-821 (2012).

Johan Baner et al., "Parallel gene analysis with allele-specific padlock probes and tag microarrays," Nucleic Acids Research, 2003, vol. 31, No. 17, e103, pp. 1-7.

(56)                    References Cited

OTHER PUBLICATIONS

Ju et al. Four-Color DNA Sequencing by Synthesis Using Cleavable Fluorescent Nucleotide Reversible Terminators. PNAS USA 103:19635-19640 (2006).

Kalivas, et al., FamRCA-RACE: a Rolling Circle Amplification Race for Isolating a Family of Homologous CDNAS in One Reaction and Its Application to Obtain Nac Genes Transcription Factors From Crocus (Crocus sativus) Flower. Preparative Biochemistry and Biotechnology 40.3 (Jul. 2010): 177-187.

Ke et al., In situ sequencing for RNA analysis in preserved tissue and cells. Nature Methods 10(9): 857 (Year: 2013).

Kim JB, Porreca GJ, Song L, Greenway SC, Gorham JM, Church GM, Seidman CE, Seidman JG. 2007. "Polony multiplex analysis of gene expression {PMAGE) in mouse hypertrophic cardiomyopathy" Science 316: 1481-4.

Klein RJ. 2007. "Power analysis for genome-wide association studies" BMC Genet 8: 58. PMC ID: PMC2042984.

Kolb HC, Finn MG, B. SK. 2001. "Click Chemistry: Diverse Chemical Function from a Few Good Reactions" Angew.Chem. Int. 40: 2004-21.

Koller, et al., Mechanisms of single-stranded phosphorothioate modified antisense oligonucleotide accumulation in hepatocytes. Nucleic Acids Research, 2011, vol. 39, No. 11, 4795-4807.

Kotewicz et al., Isolation of MMuLV RT lacking RNase H activity. Nucleic Acids Research 16(1) :265 (Year: 1988).

Kuimelis et al., Cleavage properties of an oligonucleotide containing a bridged internucleotide 5-phosphorothioate RNA linkage. Nucleic Acids Research 23 (23) : 4753-4760 (Year: 1995).

Kurimoto et al. 2007. "Global single-cell cDNA amplification to provide a template for representative high-density oligonucleotide microarray analysis" Nat Protoc 2: 739-52.

Kuznetsova et al: "What Macromolecular Crowding Can Do to a Protein". Int.J.Mol. Sci.. vol. 15. No. 12. Dec. 1, 2014 (Dec. 1, 2014). pp. 23090-23140.

Kwan et al. 2008. "Genome-wide analysis of transcript isoform variation in humans" Nat Genet 40: 225-31.

Kwiatkowski et al. 1999. "Inversion of in situ synthesized oligonucleolides: improved reagents for hybridization and primer extension in DNA microarrays" Nucleic Acids Res 27: 1710-4. PMC ID: PMC148770.

Lagunavicius et al. "Novel application of Phi29 DNA polymerase: RNA detection and analysis in vitro and in situ by target RNA-primed RCA" RNA, May 2009, 15(5), pp. 765-771.

Larsson, et al., In situ detection and genotyping of individual mRNA molecules. Nature Methods, vol. 7, No. 5, Apr. 11, 2010. pp. 395-397.

Lee, et al., "Fluorescent in situ sequencing (FISSEQ) of RNA for gene expression profiling in intact cells and tissues" Nature Protocols (Feb. 12, 2015) 10(3):442-458. XP055272042, GB ISSN:1754-2189, DOI: 10.1038/nprot.2014.191.

Lee, et al., Highly Multiplexed Subcellular RNA Sequencing in Situ. Science 343.6177 (Mar. 2014): 1360-1363, doi: 10.1126/science.1250212.

Leman, AR et al. The Replication Fork: Understanding the Eukaryotic Replication Machinery and the Challenges to Genome Duplication. Genes. Jan. 29, 2013. vol. 4; pp. 1-32; figure 1; DOI: 10.3390/genes4010001.

Leuchowius, Karl-Johan et al. Parallel Visualization of Multiple Protein Complexes in Individual Cells in Tumor Tissue. The American Society for Biochemistry and Molecular Biology, Inc. Molecular & Cellular Proteomics vol. 12, No. 6, pp. 1563-1571. Jun. 2013.

Levsky et al. "Fluorescence in situ hybridization: past, present and future" Journal of Cell Science, Jul. 15, 2003, 116 (Pt 14), pp. 2833-2838.

Levsky et al. "Single-Cell Gene Expression Profiling" Science, Aug. 2, 2002, 297(5582), pp. 836-840.

Li and Beaker. Kinetics of RNA Degradation by Specific Base Catalysis of Transesterification Involving the 2'-Hydroxyl Group. JACS 121 :5364 (Year: 1999).

Li et al. 2009. "Genome-wide Identification of Human RNA Editing Sites by Parallel DNA Capturing and Sequencing" Science in press.

Li et al. 2009. "Multiplex padlock capture and sequencing reveal human hypermulable CpG variations" Genome Res in press.

Lin et al., "CRISPR/Cas9 systems have off-target activity with insertions or deletions between target DNA and guide RNA sequences," Nucleic Acids Research, vol. 42, No. 11, pp. 7473-7485 (May 16, 2014).

Liu et al., Cell-Penetrating Peptide-Mediated Delivery of TALEN Proteins via Bioconjugation for Genome Engineering, PLOS ONE, 2014, vol. 9(1), pp. 1-7.

Lizardi, Next-generation sequencing-by-hybridization. Nature Biotechnology, vol. 26, No. 6, Jun. 2008, pp. 649-650.

Lizardi, P. M et al. Mutation detection and single-molecule counting using isothermal rolling-circle amplification. Nature genetics vol. 19,3 (1998): 225-32.

Lubeck et al. Single cell systems biology by super-resolution imaging and combinatorial labeling. Nat Methods; 9(7): 743-748. Jan. 1, 2013.

Lubeck et al., Single-cell in situ RNA profiling by sequential hybridization. Mar. 2014, Nature Methods vol. 11, No. 4, pp. 360-361.

M. Nilsson et al., "Padlock Probes: Circularizing Oligonucleotides for Localized DNA Detection," Science, vol. 25, Sep. 30, 1994, pp. 2085-2088.

Maeder, Morgan L., et al.,"Robust, synergistic regulation of human gene expression using TALE activators," Hhs Public Access Author Manuscript, vol. 10, No. 3, Feb. 10, 2013 (Feb. 10, 2013), pp. 243-245.

Mag et al. Synthesis and selective cleavage of an oligodeoxynucleotide containing a bridged internucleotide 5'-phosphorothioate linkage. Nucleic Acids Res. 19, 7 (1991): 1437-1441.

Maierhofer et al. "Multicolor Deconvolution Microscopy of Thick Biological Specimens" American Journal of Pathology, vol. 162, No. 2, Feb. 2003, pp. 373-379.

Makarova, et al. Evolution and classification of the CRISPR-Cas systems. Nat Rev Microbiol. Jun. 2011;9(6):467-77. doi: 10.1038/nrmicro2577. Epub May 9, 2011.

Mali et al., RNA-Guided Human Genome Engineering via Cas9. Science, 339 (Feb. 15, 2013): 823-826.

Mali, P. et al. CAS9 Transcriptional Activators for Target Specificity Screening and Paired Nickases for Cooperative Genome Engineering. Nature Biotechnology. Aug. 1, 2013. vol. 31; pp. 833-838; entire document. DOI: 10.1038/nbt.2675.

Marblestone, et al., Rosetta Brains: A strategy for molecularly-annotated connectomics. arXiv, Apr. 2014; 1-18.

Markaki et al. "Fluorescence In Situ Hybridization Applications for Super-Resolution 3D Structured Illumination Microscopy" Methods in Molecular Biology, Jan. 2013, vol. 950, pp. 43-64.

Mathews, CK., Biochemistry of deoxyribonucleic acid-defective amber mutants of bacteriophage T4. Journal of Biological Chemistry 243(21) :5610-5615. (Year: 1968).

Matlin, et al., Spatial Expression of the Genome: the Signal Hypothesis at Forty. Nature Reviews. Molecular Cell Biology 12.5 (May 2011): 333-340.

Mccarroll SA. 2008. "Extending genome-wide association studies to copy-number variation" Hum Mol Genet 17: R135-42.

Meade et al. "Multiplexed DNA detection using spectrally encoded porous" Analytical Chemistry, Apr. 1, 2009, 81(7), pp. 2618-2625.

Meeks, et al., Characterization of Genes Encoding Poly(a) Polymerases in Plants: Evidence for Duplication and Functional Specialization. Plos One 4.11 (Nov. 2009): e8082.

Mei, et al., A comprehensive review and performance evaluation of bioinformatics tools for HLA class I peptide-binding prediction. Briefings in bioinformatics, 00(00), 2019, 1-17.

Meng Q, Kim DH, Bai X, Bi L, Turro NJ, Ju J_ 2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.

Mignardi et al. "Fourth-generation sequencing in the cell and the clinic" Genome Medicine, 2014, 6:31.

(56)  References Cited

OTHER PUBLICATIONS

Mitra et al. 2003. "Digital genotyping and haplotyping with polymerase colonies" Proc Nall Acad Sci US A 100: 5926-31. PMC ID: PMC156303.

Mitra et al. 2003. "Fluorescent in situ sequencing on Jolymerase colonies" Anal Biochem 320: 55-65.

Mitra et al.: In situ localized amplification and contact replication of many individual DNA molecules. Nucleic Acids Res. 27(24):e34 (1999).

Moffitt, et al., Molecular, spatial, and functional single-cell profiling of the hypothalamic preoptic region. Science, Nov. 16, 2018; 362: 792-804.

Monika S Rutowska et al: "Integration of a 30 hydrogel matrix with a hollow core photonic crystal fibre for DNA probe immobilization", Measurement Science and Technology, IOP, Bristol, GB, vol. 21, No. 9, Jul. 28, 2010 (Jul. 28, 2010), p. 94016, XP020197365, ISSN: 0957-0233, DOI: 10.1088/0957-0233/21 /9/094016.

Morley M, Molony CM, Weber TM, Devlin JL, Ewens KG, Spielman RS, Cheung VG. 2004. "Genetic analysis of Genomewide variation in human gene expression" Nature 430: 743-7.

Muller et al. Towards unlimited colors for fluorescence in-situ hybridization (FISH). Chromosome Research. 10:223-232, 2002.

Nadji et ai. "Photochemically and Photoenzymatically Cleavable Dna," J. Am. Chern. Soc. 1992, 114, 9266-9269.

Nair, S. et al., Natural Killer T cells in cancer immunotherapy. Front. Immunol. Sep. 2017; 8(1178): 1-18.

Ng L et al: "Surface-based mapping of gene expression and probabilistic expression maps in the mouse cortex", Methods, Academic Press, NL, vol. 50, No. 2, Feb. 1, 2010 (Feb. 1, 2010), pp. 55-62, XP026857255, ISSN: 1 046-2023.

Nguyen, Son C.: "Strategies for Studying Chromatin Regulation and Organization", May 1, 2018 (May 1, 2018). XP055684323. Retrieved from the Internet: URL: https://dash.harvard.edu/bitstream/handle/1/33493431/NGUYEN-DISSERTATION-2016.pdf?sequence=4&isAllowed=y [retrieved on Apr. 8, 2020].

Nikolakakis, K. et al., Use of Hybridization Chain Reaction-Fluorescent In Situ Hybridization to Track Gene Expression by Both Partners during Initiation of Symbiosis. Appl Environ Microbiol . Jul. 2015;81(14):4728-35. doi: 10.1128/AEM.00890-15. Epub May 8, 2015.

Nir, Guy et al., "Walking along chromosomes with super-resolution imaging, contact maps, and integrative modeling", PLOS Genetics, vol. 14, No. 12, Dec. 26, 2018 (Dec. 26, 2018).

N.P. Gerry et al., "Universal DNA Microarray Method for Multiplex Detection of Low Abundance Point Mutations," J. Mol. Bioi. (1999), 292, 251-262, http://www.idealibrary.com.

Nuovo, G.J., Co-labeling Using In Situ PCR: A Review, Journal of Histochemistry & Cytochemistry. vol. 49. No. 11, Nov. 1, 2001 (Nov. 1, 2001). pp. 1329-1339.

Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.

Oupicky David et al: "Laterally stabilized complexes of DNA with linear reducible polycations: Strategy for triggered intracellular activation of DNA delivery vectors". Journal of the American Chemical Society. American Chemical Society. US. vol. 124. No. 1. Jan. 9, 2002 (Jan. 9, 2002). pp. 8-9.

P. Hardenbol et al., "Highly multiplexed molecular inversion probe genotyping: Over 10,000 targeted SNPs genotyped in a single tube assay," Genome Res. 2005, 15: 269-275.

P. Hardenbol et al., "Multiplexed genotyping with sequencing-tagged molecular inversion probes," Nature Biotechnology, vol. 21, No. 6, Jun. 2003, pp. 673-678.

Pan et al. 2008. "A procedure for highly specific, sensitive, and unbiased whole-genome amplification" Proc Nall Acad Sci US A 105: 15499-504. PMC ID:PMC2563063.

Parinov et al. "DNA sequencing by hybridization to microchip octa- and decanucleotides extended by stacked pentanucleotides" Nucleic Acids Research, 1996, vol. 24, No. 15, pp. 2998-3004.

Perez-Pinera, Pablo, et al., "Synergistic and tunable human gene activation by combinations of synthetic transcription factors," Nature Methods, vol. 10. No. 3, Feb. 3, 2013 (Feb. 3, 2013), pp. 239-242.

Philipp Spuhler et al: "Precise control of DNA orientation for improved functionality in protein binding microarrays", Optical MEMS and Nanophotonics (OMN), 2011 Internationalconference on, IEEE, Aug. 8, 2011 (Aug. 8, 2011), pp. 91-92,XP031968753,DOI: 10.1109/0MEMS.2011.6031084ISBN: 978-1-4577-0334-8.

PI: Piezo Nano Positioning, 2008 (online), retrieved on Aug. 12, 2020, pp. 1-6 https://www.pi -usa.us/fileadmin/user_upload/pi_us/files/product_datasheets/N725_Piezo_Focus_Positioner.pdf.

Pihlak, et al. Rapid genome sequencing with short universal tiling probes. Nature Biotechnology, 26: 676-684 (2008).

Pjanic et al. "Nuclear Factor I genomic binding associates with chromatin boundaries," BMC Genomics, Feb. 12, 2013 {Feb. 12, 2013), vol. 14, No. 99, pp. 1-18. entire document.

Polidoros, et al., Rolling circle amplification-RACE: A method for simultaneous isolation of 5' and 3' cDNA ends from amplified cDNA templates. BioTechniques 41.1 (Jul. 2006):35-42. including p. 1/1 of Supplementary Material.

Porreca et al. 2006. "Polony DNA sequencing" Curr Protoc Mol Biol Chapter 7: Unit 7.8; Supplement 76: 22 Pages.

Porreca, et al., Multiplex amplification of large sets of human exons. Nature Methods. 2007. 4: 931-6.

Qi et al. Repurposing CRISPR as an RNA-guided platform for sequence-specific control of gene expression. Cell 152:1173-1183 (2013).

Raj et al. Imaging individual mRNA molecules using multiple singly labeled probes. Nature Methods 5(10):877-879 (2008).

Ramakrishna et al. Gene disruption by cell-penetrating peptide-mediated delivery of Cas9 protein and guide RNA. Genome Research 24:1020-1027 (2014).

Ran, et al. Double Nicking by RNA-Guided CRISPR Cas9 for Enhanced Genome Editing Specificity. Cell. Aug. 2, 20138. pii: S0092-8674(13)01015-5. doi: 10.1016/j.cell.2013.08.021. [Epub ahead of print].

Rao et al., "A 3D Map of the Human Genome at Kilobase Resolution Reveals Principles of Chromatin Looping," Cell, vol. 159, No. 7, pp. 1665-1680 (Dec. 18, 2014).

Ravan, et al., Isothermal RNA Detection Through the Formation of DNA Concatemers Containing HRP-mimicking DNAzymes on the Surface of Gold Nanoparticles. Biosensors and Bioelectronics 80 (Jan. 2016): 67-73.XP029441324.

Rho, Mina et al. 'Diverse CRISPRs Evolving in Human Microbiomes.' PLoS Genetics. Vol. 8, No. 6. 1-14 pp. 1-12. Jun. 2012. entire document.

Richardson et al., Experimental and Theoretical Studies of Light-to-Heat Conversion and Collective Heating Effects in Metal Nanoparticle Solutions. Nano Letters 9(3) : 1139-1146 (Year: 2009).

Risch N, Merikangas K. 1996. "The future of genetic studies of complex human diseases" Science 273: 1516-7.

Rongqin, et al., In situ sequencing for RNA analysis in preserved tissue and cells. Nature Methods, vol. 10. No. 9. Jul. 14, 2013. pp. 857-860.

Sachidanandam et al. 2001. "A map of human genome sequence variation containing 1.42 million single nucleotide polymorphisms" Nature 409: 928-33.

Saliba, et al., Single-cell RNA-Seq: Advances and Future Challenges. Nucleic Acids Research 42.14 (2014): 8845-8860, DOI: 10.1093/nar/gku555.

Sano, et al. Immuno-PCR: Very sensitive antigen detection by means of specific antibody-DNA conjugates. Science. 258 (1992): 120-122.

Sapranauskas et al. The *Streptococcus thermophilus* CRISPR/Cas system provides immunity in *Escherichia coli*. Nucleic Acid Res. 39:9275-9282 (2011).

Schadt et al. 2003. "Genetics of gene expression surveyed in maize, mouse and man" Nature 422: 297-302.

Schadt et al. 2008. Mapping the genetic architecture of gene expression in human liver PLoS Biol 6: e107. PMC ID: PMC2365981.

Schouten et al., "Relative quantification of 40 nucleic acid sequences by multiplex ligation-dependent probe amplification," Nucleic Acids Research, 30(12):e57, 2002.

(56)        References Cited

OTHER PUBLICATIONS

Schweitzer et al. Immunoassays with rolling circle DNA amplification: a versatile platform for ultrasensitive antigen detection. Proceedings of the National Academy of Sciences. USA. 97(18) (Aug. 2000):10113-10119.

Sekhon: "Click chemistry: Current developments and applications in drug discovery" J Pharm Educ Res, vol. 3, No. 1, Jun. 1, 2012 (Jun. 1, 2012), XP055182173,* p. 80.

Seo, et al. Four-color DNA sequencing by synthesis on a chip using photocleavable fluorescent nucleotides. Proceeding of the National Academy of Sciences USA. 102.17 (Apr. 2005): 5926-5931.

Serre et al. 2008. "Differential allelic expression in the human genome: a robust approach to identify genetic and epigenetic cis-acting mechanisms regulating gene expression" PLoS Genet 4: e1000006. PMC ID: PMC2265535.

Shendure et al. 2004. "Advanced sequencing technologies: methods and goals" Nat Rev Genet 5: 335-44.

Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE. 1117839.

Shendure JA, Porreca GJ, Church GM. 2008. "Overview of DNA sequencing strategies" Curr Protec Mol Biol Chapter 7: Unit 7.1; Supplement 81: 11 Pages.

Singer-Kruger, et al., Here, There, Everywhere. RNA Biology 11.8 (Aug. 2014): 1031-1039.

Soderberg, et al., Direct Observation of Individual Endogenous Protein Complexes in Situ by Proximity Ligation. Nature Methods 3.12 (Dec. 2006): 995-1000.

Song et al., Hybridization chain reaction-based aptameric system for the highly selective and sensitive detection of protein. Analyst 137: 1396 (Year: 2012).

Sontheimer et al., "Project 7: Establishing RNA-Directed DNA Targeting in Eukaryotic Cells; Project dates: Nov. 16, 2011 to Dec. 31, 2012" (Feb. 4, 2012).

Srinivas et al., On the biophysics and kinetics of toehold-mediated DNA strand displacement. Nucleic Acids Research 41 (22) : 10641-10658 (Year: 2013).

Starnes et al., Human immunodeficiency virus reverse transcriptase-associated RNase H Activity. J. of Biological Chemistry 264(12) : 7073-7077 (Year: 1989).

Stougaard et al. 2007. "In situ detection of non-polyadenylated RNA molecules using Turtle Probes and target primed rolling circle PRINS" BMC Biotechnol 7: 69. PMC ID: PMC2203993.

Sun et al. "Composite Organic-Inorganic Nanoparticles as Raman Labels for Tissue Analysis" Nano Letters, Feb. 2007, vol. 7, No. 2, pp. 351-356.

Supplemental Material for Schweitzer et al. (PNAS 2000; 97(18):10113-10119) (Year: 2000).

Tan, et al., MicroRNA9 regulates neural stem cell differentiation by controlling Hes1 expression dynamics in the developing brain. Genes to Cells. Dec. 2012; vol. 17, Issue 12: 952-961.

Tang et al. 2009. "mRNA-Seq whole-transcriptome analysis of a single cell" Nat Methods 6: 377-82.

Terry R, Porreca G, McCarthy K, Church GM. 2008. Polonator Instrument http://www.polonator.org ; Wayback Machine(Aug. 7, 2008) "Software".

Terry R, Porreca G, McCarthy K, Church GM. 2008. Polonator Instrument http://www.polonator.org; Wayback Machine (Sep. 5, 2008) "PET {Paired End-Tag) Genomic Shotgun Library Construction Protocol".

Terry R, Porreca G, McCarthy K, Church GM. 2008. Polonator Instrument http://www.polonator.org; Wayback Machine(Aug. 7, 2008) "Flow Cells".

Terry R, Porreca G, McCarthy K, Church GM. 2008. Polonator Instrument http://www.polonator.org; Wayback Machine(Aug. 7, 2008) "Instrument Overview".

Terry R, Porreca G, McCarthy K, Church GM. 2008. Polonator Instrument http://www.polonator.org; Wayback MachineAug. 7, 2008) "Open, Affordable, Sequencing".

Terry R, Porreca G, McCarthy K, Church GM. 2008. Polonator Instrument http://www.polonator.org; Wayback Machine(Aug. 7, 2008) "Protocols".

Terry R, Porreca G, McCarthy K, Church GM. 2008. Polonator Instrument http://www.polonator.org; Wayback Machine(Aug. 7, 2008) "Reagent Kits".

Terry R, Porreca G, McCarthy K, Church GM. 2008. Polonator Instrument http://www.polonator.org; Wayback Machine(Aug. 7, 2008) "The Polonator Ecosystem".

Terry R, Porreca G, McCarthy K, Church GM. 2008. Polonator Instrument http://www.polonator.org; Wayback Machine(Aug. 7, 2008) "The Vision".

Terry R, Porreca G, McCarthy K, Church GM. 2008. Polonator Instrument http://www.polonator.org; Wayback Machine(Jul. 5, 2008) "Polony Sequence Protocols".

Terry R, Porreca G, McCarthy K, Church GM. 2008. Polonator Instrument http://www.polonator.org; Wayback Machine(Sep. 5, 2008) "Bead Capping Protocol".

Terry R, Porreca G, McCarthy K, Church GM. 2008. Polonator Instrument http://www.polonator.org; Wayback Machine(Sep. 5, 2008) "Bead Enrichment Protocol".

Terry R, Porreca G, McCarthy K, Church GM. 2008. Polonator Instrument http://www.polonator.org; Wayback Machine(Sep. 5, 2008) "Coverslip Aminosilanation and Arraying Protocol".

Terry R, Porreca G, McCarthy K, Church GM. 2008. Polonator Instrument http://www.polonator.org; Wayback Machine(Sep. 5, 2008) "Emulsion Breaking Protocol".

Terry R, Porreca G, McCarthy K, Church GM. 2008. Polonator Instrument http://www.polonator.org; Wayback Machine(Sep. 5, 2008) "Emulsion PCR Protocol".

Terry R, Porreca G, McCarthy K, Church GM. 2008. Polonator Instrument http://www.polonator.org; Wayback Machine(Sep. 5, 2008) "Emulsion PCR/Bead Capping Kits".

Terry R, Porreca G, McCarthy K, Church GM. 2008. Polonator Instrument http://www.polonator.org; Wayback Machine(Sep. 5, 2008) "Enrichment Kits".

Terry R, Porreca G, McCarthy K, Church GM. 2008. Polonator Instrument http://www.polonator.org; Wayback Machine(Sep. 5, 2008) "Help Wanted".

Terry R, Porreca G, McCarthy K, Church GM. 2008. Polonator Instrument http://www.polonator.org; Wayback Machine(Sep. 5, 2008) "Paired-Leg Library Kits".

Terry R, Porreca G, McCarthy K, Church GM. 2008. Polonator Instrument http://www.polonator.org; Wayback Machine(Sep. 5, 2008) "Polony Sequence by Ligation Protocol".

Terry R, Porreca G, McCarthy K, Church GM. 2008. Polonator Instrument http://www.polonator.org; Wayback Machine(Sep. 5, 2008) "Run Kits".

The Delivery Problem, Nature Biotechnology, 2006, vol. 24(3), pp. 305-306.

Thisse et al., High-resolution in Situ Hybridization to Whole-mount Zebrafish Embryos. Nature Protocols 3.1 (2008): 59-69, Doi:10. 1038/nprot.2007.514.

Tiley, LS et al. The VP16 Transcription Activation Domain Is Functional When Targeted to a Promoter-Proximal RNA Sequence. Genes and Development. 1992. vol. 6; pp. 2077-2087; abstract; p. 2077, first column, first paragraph.

Tillberg, et al., Protein-retention expansion microscopy of cells and tissues labeled using standard fluorescent proteins and antibodies. Nat Biotechnol . Sep. 2016;34(9):987-92. doi: 10.1038/nbt.3625. Epub Jul. 4, 2016.

Trafton, A. Editing The Genome With High Precision [online]. MIT News office. Jan. 3, 2013 [retrieved on Dec. 4, 2014). Retrieved from the Internet: URL: https://news.mit.edu/2013/editing-the-genome-with-high-precision-0103 ;pp. 1-3; p. 3, third paragraph.

Tran et al. "A Universal DNA-Based Protein Detection System," Journal of American Chemical Society, Sep. 25, 2013 {Sep. 25, 2013), vol. 135, No. 38, p. 14008-14011 and Supporting Information. entire document.

Tsaflaris, et al., Isolation of Three Homologous AP1-like MADS-box Genes in Crocus (*Crocus sativus* L.) and Characterization of Their Expression. Plant Science 166.5 (May 2004): 1235-1243.

(56) References Cited

OTHER PUBLICATIONS

Vigneault F, Sismour AM, Church GM. 2008." Efficient microRNA capture and bar-coding via enzymatic oligonucleotide adenylation" Nat Methods 5: 777-9.

Wang, et al., Rapid and Sensitive detection of severe acute respiratory syndrome coronavirus by rolling circle amplification, 2005,43, 2339-2344.

Wang, et al. RNA-Seq: a revolutionary tool for transcriptomics. Nature Reviews Genetics, 10: 57-63 (2009).

Wang et al., "The method of axial drift compensation of laser differential confocal microscopy based on zero-tracking," Proc. of SPIE, vol. 9618, 96180X (2015).

Wählby et al. Sequential immunofluorescence staining and image analysis for detection of large numbers of antigens in individual cell nuclei. 47(1):32-41 (2002).

Weibrecht, et al., Simultaneous Visualization of Both Signaling Cascade Activity and End-Point Gene Expression in Single Cells, PLOS ONE. vol. 6. No. 5, May 25, 2011. p. e20148.

Weis, et al., Protein Targeting to Subcellular Organelles via mRNA Localization. Biochimica et Biophysica Acta 1833 available online (Apr. 2012): 260-273.

Wiedenheft et al. RNA-guided genetic silencing systems in bacteria and archaea. Nature 482:331-338 (2012).

Wilson et al. "Encoded Microcarriers for High-Throughput Multiplexed Detection" Angewandte Chemie International Edition, Sep. 18, 2006, 45(37), pp. 6104-6117.

Wright et al., "Dynamic closed-loop system for focus tracking using a spatial light modulator and a deformable membrane mirror," Optics Express, vol. 14, No. 1, pp. 222-228 (Jan. 9, 2006).

Wu et al.., "3'-o-modified Nucleotides as Reversible Terminators for Pyrosequencing," PNA, 2007, vol. 104(42), pp. 16462-16467.

Xiao et al., "Single-step Electronic Detection of Femtomolar DNA by Target-induced Strand Displacement in an Electrode-bound Duplex," PNAS, 2006, vol. 103(45), pp. 16677-16680.

Yamaguchi et al. "eDNA display: a novel screening method for functional disulfide-rich peptides by solid-phase synthesis and stabilization of mRNA-protein fusions," Nucleic Acids Research, Jun. 15, 2009 {Jun. 15, 2009), vol. 37, No. 16, e108 {p. 1-13 for citations). entire document.

Yaroslavsky, et al. Fluorescence imaging of single-copy DNA sequences within the human genome using PNA-directed padlock probe assembly. Chemistry & biology 2013, 20(3):445-453; Abstract, p. 447, Figure 1 and its legend; p. 448, Table 1.

Y. Wang et ai., "Allele quantification using molecular inversion probes {MIP)," Nucleic Acids Research, 2005, vol. 33, No. 21, e183,pp. 1-14.

Zhang et al. 2006. "Long-range polony haplotyping of individual human chromosome molecules" Nat Genet 38: 382-7.

Zhang et al., "Digital RNA Allelotyping Reveals Tissue-specific and Allele-specific Gene Expression in Human," Nat Methods., Aug. 2009, vol. 6(8), pp. 613-618.

Zhang et al., Dynamic DNA nanotechnology using strand-displacement reactions. Nature Chemistry 3 : 103-113 (Year: 2011).

Zhang et al., "Sequencing Genomes From Single Cells by Polymerase Cloning," Nature Biotechnology, 2006, vol. 24(6), pp. 680-686.

Zhao et al. "Advances of multiplex and high throughput biomolecular detection technologies based on encoding microparticles" Science China Chemistry, Aug. 2011, vol. 54, No. 8, pp. 1185-1201.

Zhao et al., An electrochemical aptasensor based on hybridization chain reaction with enzyme-signal amplification for interferon-gamma detection. Biosensors and Bioelectronics 36: 129-134 (Year: 2012).

Zhou, et al., In Situ detection of Messenger RNA using digoxiogenin-labeled oligonucleotides and rolling circle amplification. Experimental and molecular Pathology, 2001; 70: 281-288.

International HapMap C. 2005. "A haplotype map of the human genome" Nature 437: 1299-320 (2005).

Ren et al., Azide and trans-cyclooctene dUTPs: incorporation into DNA probes and fluorescent click-labelling. The Analyst, 140:(8) 2671-2678 (2015). DOI: 10.1039/c5an00158g.

Thomas et al., A Computer-controlled Nanosecond Laser. Computers in Chemistry, 22(6): 491-98 (1998).

* cited by examiner

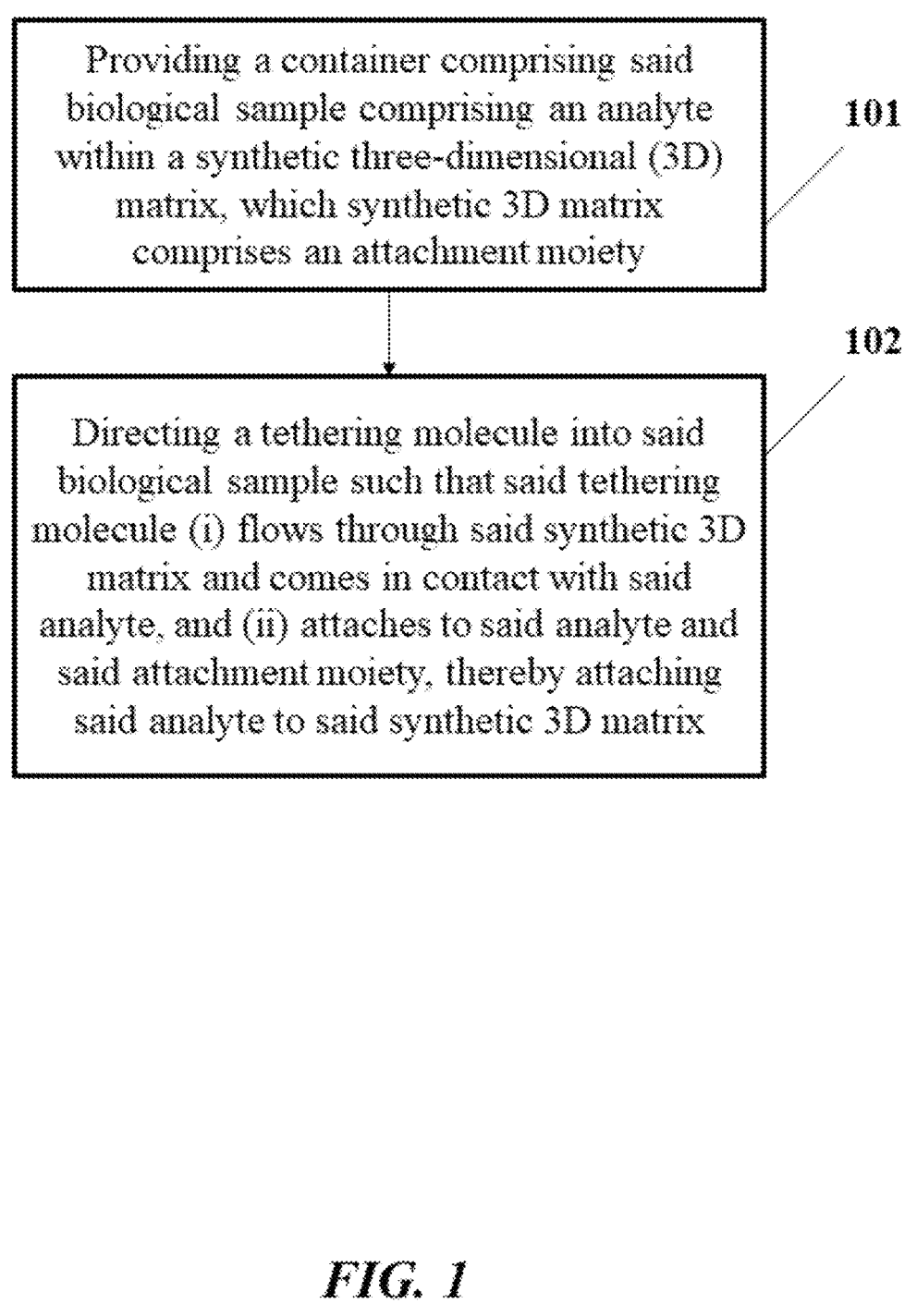

Providing a container comprising said biological sample comprising an analyte within a synthetic three-dimensional (3D) matrix, which synthetic 3D matrix comprises an attachment moiety

101

102

Directing a tethering molecule into said biological sample such that said tethering molecule (i) flows through said synthetic 3D matrix and comes in contact with said analyte, and (ii) attaches to said analyte and said attachment moiety, thereby attaching said analyte to said synthetic 3D matrix

*FIG. 1*

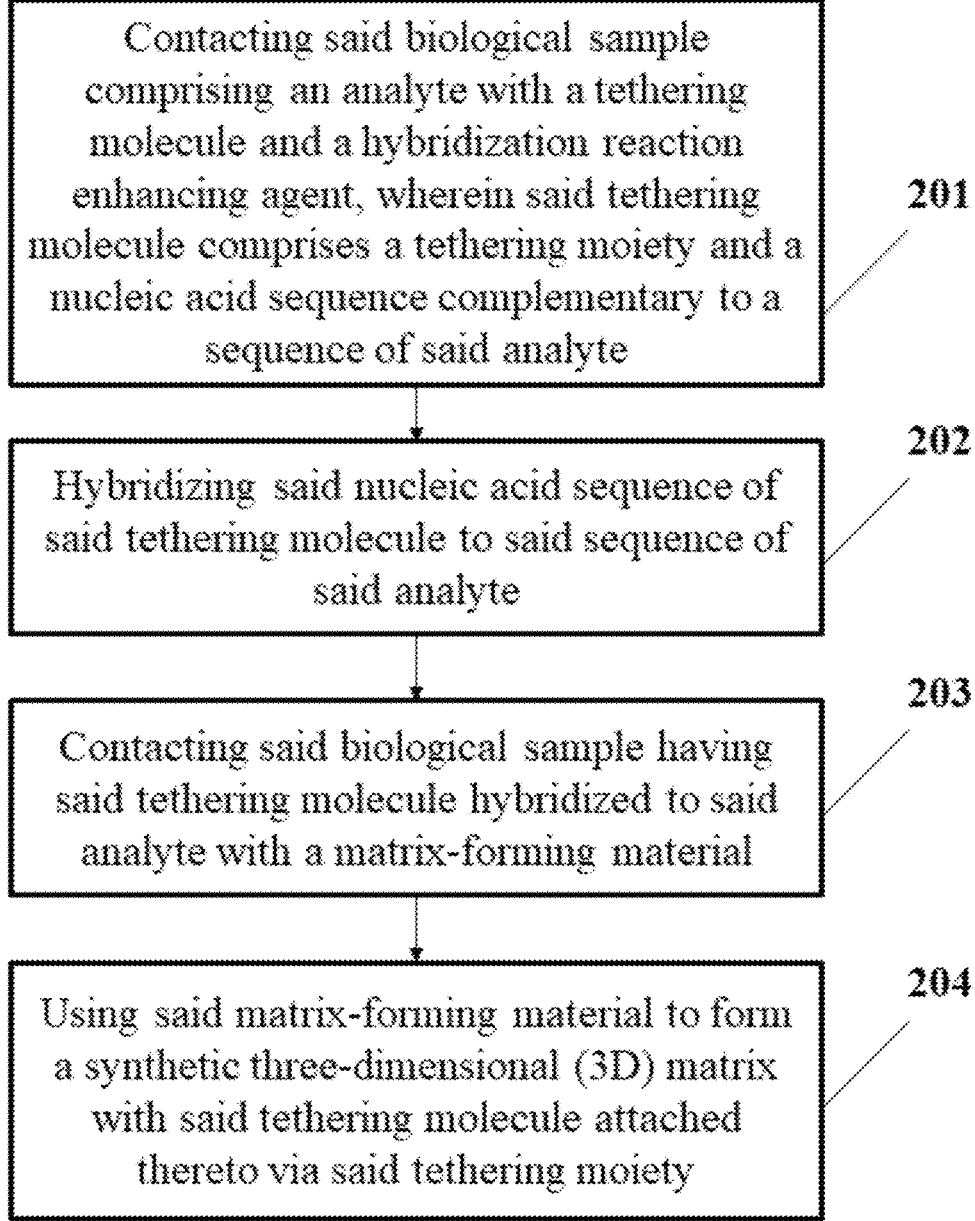

Contacting said biological sample comprising an analyte with a tethering molecule and a hybridization reaction enhancing agent, wherein said tethering molecule comprises a tethering moiety and a nucleic acid sequence complementary to a sequence of said analyte — 201

Hybridizing said nucleic acid sequence of said tethering molecule to said sequence of said analyte — 202

Contacting said biological sample having said tethering molecule hybridized to said analyte with a matrix-forming material — 203

Using said matrix-forming material to form a synthetic three-dimensional (3D) matrix with said tethering molecule attached thereto via said tethering moiety — 204

A)
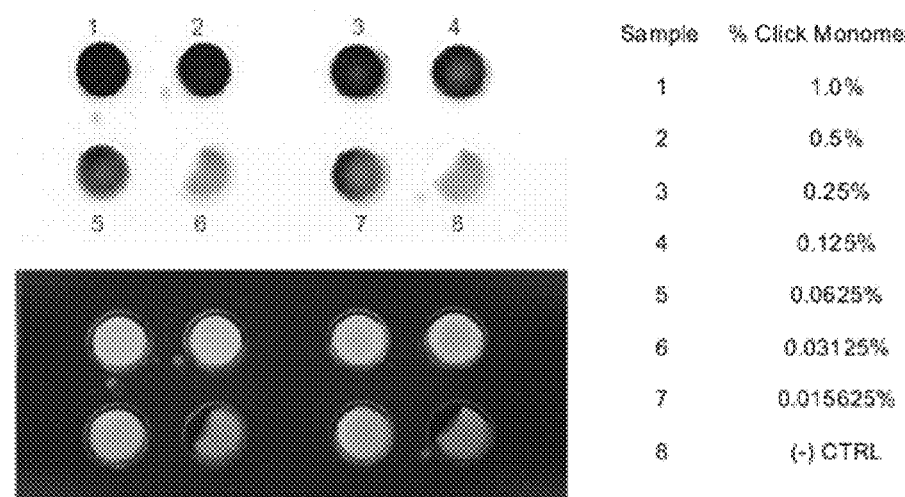
| Sample | % Click Monomer |
|--------|-----------------|
| 1 | 1.0% |
| 2 | 0.5% |
| 3 | 0.25% |
| 4 | 0.125% |
| 5 | 0.0625% |
| 6 | 0.03125% |
| 7 | 0.015625% |
| 8 | (-) CTRL |
B)
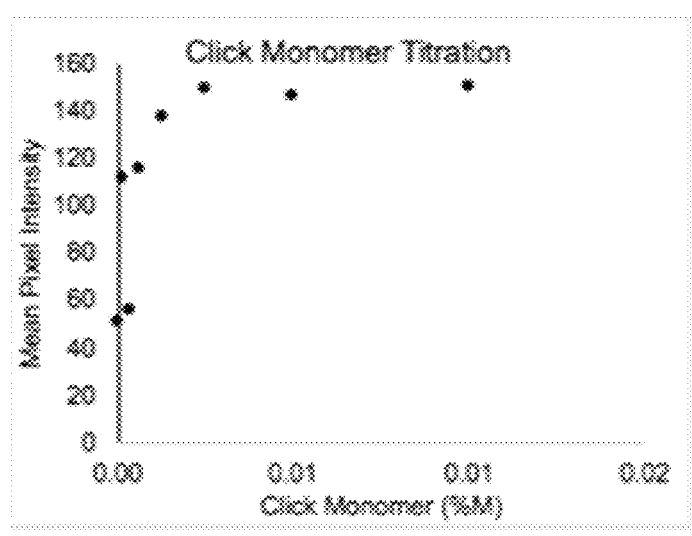
FIG. 5

A)

B)

A)
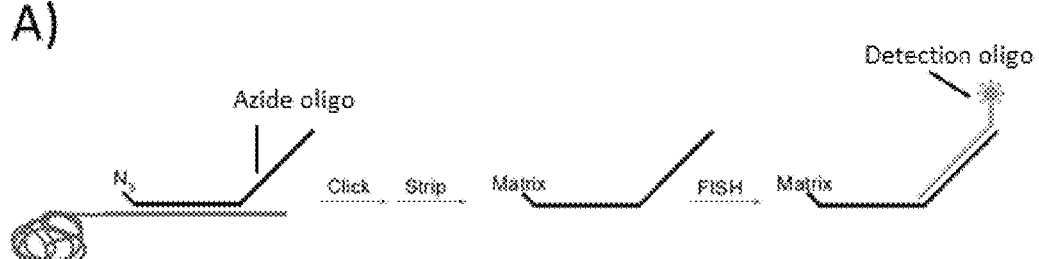
B)
C)
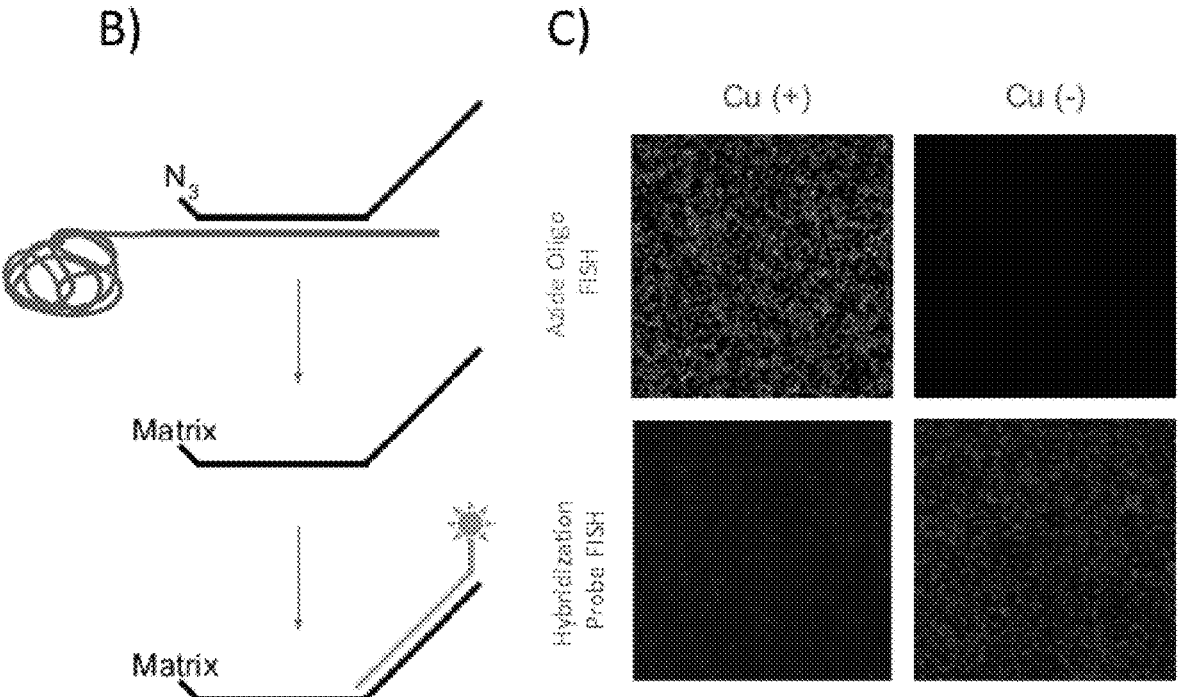
FIG. 7

COMPOSITIONS AND METHODS FOR ANALYTE DETECTION

CROSS-REFERENCE

This application is a continuation of International Application No. PCT/US21/15578, filed Jan. 28, 2021 which claims priority to U.S. Provisional Patent Application No. 62/967,362, filed Jan. 29, 2020, which application is herein incorporated by reference in its entirety for all purposes.

BACKGROUND

Fluorescent in situ sequencing (FISSEQ) can be used to detect target molecules within a sample (e.g., a biological sample) in situ. During FISSEQ, a three-dimensional (3D) matrix can be generated within the sample to immobilize the target molecules or derivatives thereof. Nucleic acid target molecules may be subsequently amplified and sequenced within the 3D matrix. The 3D matrix with the attached nucleic acid molecules can provide an information storage medium where the nucleic acid molecules represent stored information which can be read within the 3D matrix.

FISSEQ may be used to detect one or more fluorescent signals emanating from each sequencing template within a FISSEQ library over more than one cycle of fluorescence detection, wherein the fluorescent signals over the totality of detection cycles may comprise an information construct, which may be mapped to molecular identification or otherwise provide information about the nature of the detected molecule. The 3D matrix can allow reagent exchange and removal of background molecules without losing the target molecules.

SUMMARY

Recognized herein is a need for a robust protocol for processing a sample for fluorescent in situ sequencing (FISSEQ). The methods and systems provided herein can be used to immobilize target nucleic acid molecules on the three-dimensional (3D) matrix and allow efficient buffer exchange and clearing of background molecules within the 3D matrix.

In an aspect, the present disclosure provides a method for processing a biological sample, comprising: (a) providing a container comprising the biological sample comprising an analyte within a synthetic three-dimensional (3D) matrix, which synthetic 3D matrix comprises an attachment moiety; and (b) directing a tethering molecule into the biological sample such that the tethering molecule (i) flows through the synthetic 3D matrix and comes in contact with the analyte, and (ii) attaches to the analyte and the attachment moiety, thereby attaching the analyte to the synthetic 3D matrix.

In some embodiments, the tethering molecule comprises a tethering moiety that has specificity for the attachment moiety. In some embodiments, the synthetic 3D matrix encapsulates the biological sample. In some embodiments, the method further comprises, prior to (a), providing a matrix-forming material in the container, and using the matrix-forming material to generate the synthetic 3D matrix. In some embodiments, the synthetic 3D matrix is generated by polymerization of the matrix-forming material. In some embodiments, the synthetic 3D matrix is generated by cross-linking of the matrix-forming material. In some embodiments, the method further comprises, subsequent to (b), identifying the analyte within the synthetic 3D matrix. In some embodiments, the tethering molecule comprises a nucleic acid sequence complementary to a sequence of the analyte. In some embodiments, the tethering molecule comprises a poly-deoxythymidine (dT) sequence. In some embodiments, the method further comprises, in (b), contacting the biological sample with a hybridization reaction enhancing agent, wherein the hybridization reaction enhancing agent enhances a rate of hybridization between the nucleic acid sequence and the sequence of the analyte. In some embodiments, the hybridization reaction enhancing agent comprises a functional group that facilitates inactivation of the hybridization reaction enhancing agent. In some embodiments, the method further comprises subsequent to contacting the biological sample with the hybridization reaction enhancing agent, subjecting the functional group to conditions sufficient to inactivate the hybridization reaction enhancing agent. In some embodiments, the method further comprises inactivating the hybridization reaction enhancing agent. In some embodiments, the functional group is a hydrating group. In some embodiments, the hydrating group is an ionic, electrolytic, or hydrophilic group. In some embodiments, the functional group further comprises a cleavable linker, which cleavable linker links the functional group to a polymer backbone of the hybridization reaction enhancing agent. In some embodiments, the cleavable linker comprises an alpha-hydroxy acid, a beta-keto acid, or a disulfide linkage. In some embodiments, the method further comprises cleaving the functional group from the polymer backbone of the hybridization reaction enhancing agent. In some embodiments, the method further comprises removing the functional group from the synthetic 3D matrix. In some embodiments, the method further comprises removing the hybridization reaction enhancing agent from the synthetic 3D matrix. In some embodiments, the removing comprises washing away the hybridization reaction enhancing agent from the synthetic 3D matrix. In some embodiments, the method further comprises, subsequent to (b), contacting the biological sample encapsulated within the synthetic 3D matrix with a protease. In some embodiments, the analyte is (i) a nucleic acid molecule or (ii) a polypeptide molecule. In some embodiments, the analyte is one or more polypeptide molecules, wherein the analyte is bound by an antibody or fragment thereof. In some embodiments, the antibody or fragment thereof is conjugated to a nucleic acid barcode, and wherein the tethering molecule comprises a nucleic acid sequence complementary to the nucleic acid barcode. In some embodiments, the analyte is one or more polypeptide molecules, and wherein the tethering molecule is an antibody or fragment thereof conjugated to a nucleic acid barcode. In some embodiments, the nucleic acid barcode comprises a tethering moiety, which tethering moiety attaches to the attachment moiety of the synthetic 3D matrix.

In some embodiments, the analyte is the nucleic acid molecule, and wherein the tethering molecule comprises a primer sequence complementary to a sequence of a nucleic acid molecule of the one or more nucleic acid molecules. In some embodiments, the method further comprises, in (b), hybridizing the primer sequence to the sequence of the nucleic acid molecule. In some embodiments, the method further comprises, subsequent to (b), extending the primer sequence hybridized to the sequence of the nucleic acid molecule to generate an extension product attached to the synthetic 3D matrix. In some embodiments, the method further comprises hybridizing a probe to the extension product in presence of an additional hybridization reaction enhancing agent. In some embodiments, the probe is a padlock probe or a molecular inversion probe. In some embodiments, the method further comprises inactivating the additional hybridization reaction enhancing agent or remov-ing the additional hybridization reaction enhancing agent from the synthetic 3D matrix. In some embodiments, the method further comprises circularizing the probe. In some embodiments, the circularizing comprises ligating a 3' end and a 5' end of the probe. In some embodiments, the method further comprises subjecting the probe to an amplification reaction to generate an amplification product. In some embodiments, the amplification reaction is rolling circle amplification. In some embodiments, the amplification reac-tion incorporates a modified base to the amplification prod-uct. In some embodiments, the modified base is 5-azidom-ethyl-dUTP. In some embodiments, the amplification reaction is a non-enzymatic reaction. In some embodiments, the non-enzymatic reaction is a hybridization chain reaction (HCR) or a branched DNA reaction. In some embodiments, the biological sample is a cell or a tissue. In some embodi-ments, the cell or the tissue is fixed. In some embodiments, the cell or the tissue is permeabilized.

In another aspect, the present disclosure provides a method for processing a biological sample, comprising: (a) contacting the biological sample comprising an analyte with a tethering molecule and a hybridization reaction enhancing agent, wherein the tethering molecule comprises a tethering moiety and a nucleic acid sequence complementary to a sequence of the analyte, and wherein the hybridization reaction enhancing agent enhances a rate of hybridization between the nucleic acid sequence and the sequence of the analyte; (b) hybridizing the nucleic acid sequence of the tethering molecule to the sequence of the analyte; (c) contacting the biological sample having the tethering mol-ecule hybridized to the analyte with a matrix-forming mate-rial; and (d) using the matrix-forming material to form a synthetic three-dimensional (3D) matrix with the tethering molecule attached thereto via the tethering moiety.

In some embodiments, the synthetic 3D matrix preserves an absolute or relative spatial position of the analyte within the biological sample. In some embodiments, the synthetic 3D matrix preserves an absolute or relative spatial position of a molecule that can be associated with the analyte within the biological sample (e.g., a preserve the location of a derivative of the analyte or a nucleic acid molecule coupled to a binding agent that bound the analyte). In some embodi-ments, the synthetic 3D matrix further comprises an attach-ment moiety. In some embodiments, the tethering moiety of the tethering molecule has specificity for the attachment moiety. In some embodiments, the method further com-prises, in (d), attaching the tethering moiety to the attach-ment moiety. In some embodiments, the hybridization reac-tion enhancing agent comprises a functional group that facilitates inactivation of the hybridization reaction enhanc-ing agent. In some embodiments, the method further com-prises, subsequent to (d), subjecting the functional group to conditions sufficient to inactivate the hybridization reaction enhancing agent. In some embodiments, the method further comprises inactivating the hybridization reaction enhancing agent. In some embodiments, the functional group is a hydrating group. In some embodiments, the hydrating group is an ionic, electrolytic, or hydrophilic group. In some embodiments, the functional group further comprises a cleavable linker, which cleavable linker links the functional group to a polymer backbone of the hybridization reaction enhancing agent. In some embodiments, the cleavable linker comprises an alpha-hydroxy acid, a beta-keto acid, or a disulfide linkage. In some embodiments, the method further comprises cleaving the functional group from the polymer backbone of the hybridization reaction enhancing agent. In some embodiments, the method further comprises removing the functional group from the synthetic 3D matrix. In some embodiments, the method further comprises removing the hybridization reaction enhancing agent from the synthetic 3D matrix. In some embodiments, the removing comprises washing away the hybridization reaction enhancing agent from the synthetic 3D matrix. In some embodiments, the method further comprises, subsequent to (d), contacting the biological sample encapsulated within the synthetic 3D matrix with a protease. In some embodiments, the analyte is (i) a nucleic acid molecule or (ii) a polypeptide molecule. In some embodiments, the analyte is one or more polypeptide molecules, wherein the analyte is bound by an antibody or fragment thereof. In some embodiments, the antibody or fragment thereof is conjugated to a nucleic acid barcode, and wherein the tethering molecule comprises a nucleic acid sequence complementary to the nucleic acid barcode. In some embodiments, the analyte is one or more nucleic acid molecules, and wherein the tethering molecule comprises a primer sequence complementary to a sequence of a nucleic acid molecule of the one or more nucleic acid molecules. In some embodiments, the method further comprises, subse-quent to (d), extending the primer sequence hybridized to the sequence of the nucleic acid molecule to generate an exten-sion product attached to the synthetic 3D matrix. In some embodiments, the method further comprises hybridizing a probe to the extension product in presence of an additional hybridization reaction enhancing agent. In some embodi-ments, the probe is a padlock probe or a molecular inversion probe. In some embodiments, the method further comprises inactivating the additional hybridization reaction enhancing agent or removing the additional hybridization reaction enhancing agent from the synthetic 3D matrix. In some embodiments, the method further comprises circularizing the probe. In some embodiments, the circularizing com-prises ligating a 3' end and a 5' end of the probe. In some embodiments, the method further comprises subjecting the probe to an amplification reaction to generate an amplifica-tion product. In some embodiments, the amplification reac-tion is rolling circle amplification. In some embodiments, the amplification reaction incorporates a modified base to the amplification product. In some embodiments, the modi-fied base is 5-azidomethyl-dUTP. In some embodiments, the amplification reaction is a non-enzymatic reaction. In some embodiments, the non-enzymatic reaction is a hybridization chain reaction (HCR) or a branched DNA reaction. In some embodiments, the biological sample is a cell or a tissue. In some embodiments, the cell or the tissue is fixed. In some embodiments, the cell or the tissue is permeabilized.

In another aspect, the present disclosure provides a com-position for processing a biological sample comprising an analyte, comprising: the biological sample encapsulated within a synthetic three-dimensional (3D) matrix; an attach-ment moiety coupled to the synthetic 3D matrix; a tethering probe, wherein the tethering probe comprises a nucleic acid sequence complementary to a sequence of the analyte, and wherein the nucleic acid sequence is configured to hybridize to the sequence of the analyte; and a hybridization reaction enhancing agent, which hybridization reaction enhancing agent enhances a rate of hybridization between the nucleic acid sequence and the sequence of the analyte. In some embodiments, the attachment moiety is configured to pre-serve an absolute or relative spatial position of the analyte within the synthetic 3D matrix.

In some embodiments, the analyte is a nucleic acid molecule or a polypeptide molecule. In some embodiments, the biological sample is a cell or a tissue. In some embodiments, the cell or the tissue is fixed. In some embodiments, the cell or the tissue is permeabilized. In some embodiments, the hybridization reaction enhancing agent comprises a functional group that facilitates inactivation of the hybridization reaction enhancing agent. In some embodiments, the functional group is a hydrating group. In some embodiments, the hydrating group is an ionic, electrolytic, or hydrophilic group. In some embodiments, the functional group further comprises a cleavable linker, which cleavable linker links the functional group to a polymer backbone of the hybridization reaction enhancing agent.

In another aspect, the present disclosure provides a method for processing a biological sample, comprising: (a) contacting the biological sample comprising a polypeptide analyte with a tethering molecule, wherein the tethering molecule comprises (i) an antibody or fragment thereof conjugated to a nucleic acid barcode and (ii) a tethering moiety; (b) binding the polypeptide analyte with the tethering molecule; (c) contacting the biological sample having the tethering molecule bound to the polypeptide analyte with a matrix-forming material; and (d) using the matrix-forming material to form a synthetic three-dimensional (3D) matrix with the tethering molecule attached thereto via the tethering moiety.

In another aspect, the present disclosure provides a method for processing a biological sample, comprising providing the biological sample comprising a polypeptide analyte within a synthetic three-dimensional (3D) matrix, which synthetic 3D matrix comprises an attachment moiety; contacting the biological sample with a tethering molecule, wherein the tethering molecule comprises (i) an antibody or fragment thereof conjugated to a nucleic acid barcode and (ii) a tethering moiety; and binding the polypeptide analyte with the tethering molecule; thereby attaching the analyte to the synthetic 3D matrix via the attachment moiety.

In some of any such embodiments, the biological sample may comprise an additional analyte within the synthetic 3D matrix. In some embodiments, the synthetic 3D matrix comprises an additional attachment moiety. In some cases, one or more additional attachment moieties are provided to the synthetic 3D matrix after it is formed. In some cases, one or more additional attachment moieties are provided to the synthetic 3D matrix before or during it is formed. In some cases, contacting said biological sample with a tethering molecule is performed simultaneously or concurrently with forming of the synthetic 3D matrix. In some cases, contacting said biological sample with a tethering molecule is performed after forming of the synthetic 3D matrix. In some embodiments, the additional analyte is a nucleic acid molecule.

In some of any such embodiments, the method includes providing an additional tethering molecule, wherein the additional tethering molecule comprises a primer sequence complementary to a sequence of the nucleic acid molecule. In some aspects, the method includes hybridizing the primer sequence to the sequence of the nucleic acid molecule. In some examples, the method includes extending the primer sequence hybridized to the sequence of the nucleic acid molecule to generate an extension product. In some embodiments, the extension product can be attached to the synthetic 3D matrix.

In some embodiments, the method includes hybridizing a probe to the extension product. In some examples, the probe is a padlock probe or a molecular inversion probe. In some cases, the method includes circularizing the probe. In some example, circularizing comprises ligating a 3' end and a 5' end of the probe. In some embodiments, the probe is subjected to an amplification reaction to generate an amplification product. In some examples, the amplification reaction is rolling circle amplification. In some embodiments, the amplification reaction incorporates a modified base to the amplification product. In some cases, the modified base is 5-azidomethyl-dUTP.

In some of any such embodiments, the attachment moiety and the additional attachment moiety are different. For example, in some instances, the tethering moiety comprises an acryloyl group and the additional tethering moiety is an azide. In some embodiments the additional tethering molecule (i) flows through the synthetic 3D matrix and comes in contact with the additional analyte, and (ii) attaches to the additional analyte and the additional attachment moiety, thereby attaching the additional analyte to the synthetic 3D matrix.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference, to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1 shows an example procedure for processing a sample using a method described herein.

FIG. 2 shows an example procedure for processing a sample using a method described herein.

FIG. 4 (panel A) shows an example of click chemistry described herein and FIG. 4 (panel B) shows an example reagent described herein.

FIG. 5 (panel A) shows an example of click monomer titration and FIG. 5 (panel B) shows graphed results described herein.

FIG. 7A, FIG. 7B and FIG. 7C show examples of azide probe tethering using a method described herein.

DETAILED DESCRIPTION

Figure 3:
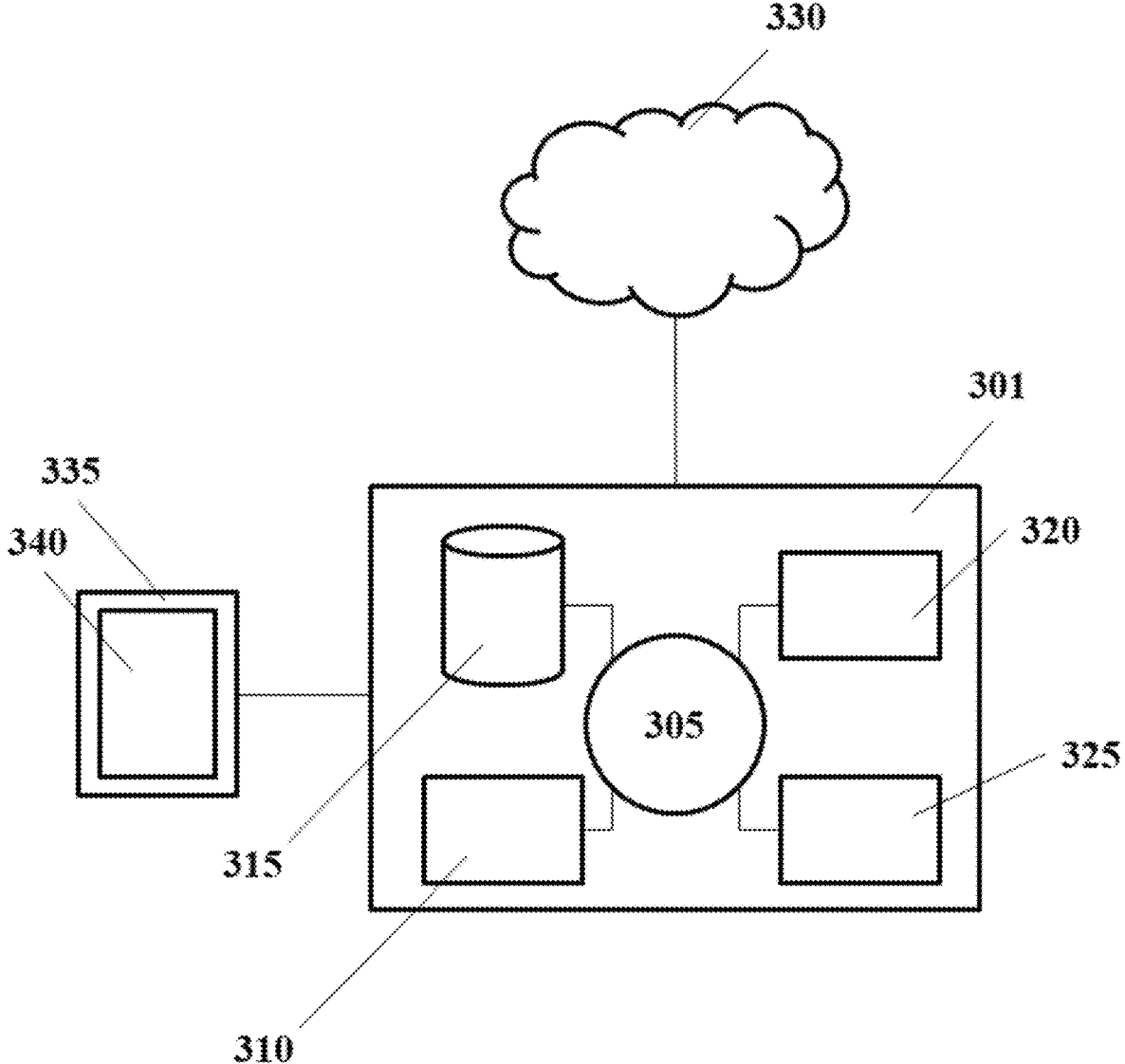
FIG. 3 shows a computer system that is programmed or otherwise configured to implement methods provided herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "nucleic acid," as used herein, generally refers to a nucleic acid molecule comprising a plurality of nucleotides or nucleotide analogs. A nucleic acid may be a polymeric form of nucleotides. A nucleic acid may comprise deoxyribonucleotides, ribonucleotides, analogs thereof, or a combination thereof. A nucleic acid may be an oligonucleotide or a polynucleotide. Nucleic acids may have various three-dimensional structures and may perform various functions. Non-limiting examples of nucleic acids include DNA, RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation, with a functional moiety for immobilization.

The terms "polypeptide" and "peptide" are used interchangeably herein, and they refer to a polymeric form of amino acids. A polypeptide can comprise two or more amino acids. A polypeptide can be unstructured or structured. A polypeptide can be a protein.

The term "rolony," as used herein, generally refers to a rolling circle colony, such as, for example, a colony of nucleic acid molecules generated by rolling circle amplification (RCA).

The terms "amplifying" and "amplification" generally refer to generating one or more copies (or "amplified product" or "amplification product") of a nucleic acid. The one or more copies may be generated by nucleic acid extension. Such extension may be a single round of extension or multiple rounds of extension. The amplified product may be generated by polymerase chain reaction (PCR).

Methods for Sample Processing

The present disclosure provides methods for processing a sample, e.g., a biological sample. In some aspects, the method can comprise providing a container comprising a biological sample comprising an analyte within a three-dimensional (3D) matrix. The 3D matrix can be a synthetic 3D matrix. For example, the 3D matrix can be generated by polymerizing or crosslinking a matrix-forming material comprising matrix-forming monomers or polymers. The 3D matrix can encapsulate the sample. The 3D matrix can comprise an attachment moiety for immobilizing analytes. The analyte can be a nucleic acid molecule, a polypeptide molecule, a small molecule or a combination thereof. Next, a tethering molecule may be directed into the sample through the 3D matrix and in contact with the analyte. The tethering molecule may attach to the analyte and the attachment moiety, thereby attaching the analyte to the 3D matrix. The tethering molecule can comprise a tethering moiety that has specificity for the attachment moiety. The tethering moiety and the attachment moiety can be a protein-protein binding pair or functional moieties that can react with each other. For example, the tethering moiety can be an amine, a thiol, an azide, an alkyne, a nitrone, an alkene, a tetrazine, a tetrazole, an acrydite or other click reactive group. The tethering molecule can comprise a nucleic acid sequence complementary to a sequence of the analyte. For example, the tethering molecule can comprise a poly-deoxythymidine (dT) sequence. Next, the analyte can be detected within the 3D matrix. Detection methods can be various methods described herein, including but not limited to, hybridization with labeled probes and sequencing.

The sample within the 3D matrix can be contacted with a hybridization reaction enhancing agent. The hybridization reaction enhancing agent can enhance a rate of hybridization between the nucleic acid sequence and the sequence of the analyte. The hybridization reaction enhancing agent can comprise a functional group that facilitates inactivation of the hybridization reaction enhancing agent. The functional group can be subjected to conditions sufficient to inactivate the hybridization reaction enhancing agent. The hybridization reaction enhancing agent can be inactivated. The functional group can be a hydrating group. For example, the hydrating group can be an ionic, electrolytic, or hydrophilic group. The functional group can further comprise a cleavable linker. The cleavable linker can link the functional group to a polymer backbone of the hybridization reaction enhancing agent. The cleavable linker can comprise an alpha-hydroxy acid, a beta-keto acid, or a disulfide linkage. The functional group may be cleaved from the polymer backbone of the hybridization reaction enhancing agent. The functional group may be removed from the 3D matrix. In some cases, the functional group can be washed away from the 3D matrix by a buffer. The hybridization reaction enhancing agent may also be removed from the 3D matrix. For example, the hybridization reaction enhancing agent can be washed away from the 3D matrix. In some embodiments, the hybridization reaction enhancing agent is not dextran sulfate. Moreover, enhancing agents described herein, including, for example, smaller enhancing reagents, may be inactivated by washing them away from the 3D matrix.

In some cases, the biological sample encapsulated within the 3D matrix can be subjected to a clearing process. The biological sample encapsulated within the 3D matrix can be contacted with an agent to clear the sample and fully permeabilize the sample. For example, the biological sample can be contacted with a protease to break down proteins. Other examples of agents used to break down non-target molecules includes, but are not limited to, detergents, organic solvents and denaturants. In some embodiments, a clearing agent is applied to the sample after the tethering molecule(s) directly or indirectly bound or attached to an analyte (or a derivative thereof) is bound or linked to the 3D matrix. In some embodiments, a clearing agent is applied to the sample after the tethering moiety directly or indirectly bound or attached to an analyte (or a derivative thereof) is bound or linked to the attachment moiety of the 3D matrix.

The analyte can be various molecules. The analyte can be one or more nucleic acid molecules or one or more polypeptide molecules. In some cases, the analyte is a polypeptide molecule, and the analyte can be bound by a binding agent (e.g., an antibody or antibody fragment) conjugated to a reporter sequence that identifies the binding agent (e.g., a nucleic acid barcode). In some embodiments, the reporter sequence that identifies the binding agent, can be targeted for analysis. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide. In some cases, the analyte is a nucleic acid hybridized to a nucleic acid barcode. In some embodiments, an antibody or antibody fragment conjugated to a nucleic acid barcode, or the conjugated barcode itself, is the analyte and a nucleic acid hybridized to the nucleic acid barcode, such as a nucleic acid probe or a derivative thereof (e.g., wherein the nucleic acid probe can be circularized, ligated, and amplified to form a RCA such as a rolony), is the tethering molecule. In some embodiments, an amplification product (e.g., a RCA product such as a rolony) comprises functional moieties for immobilization and is the tethering molecule. In some embodiments, the nucleic acid probe for hybridizing to the nucleic acid barcode conjugated to an antibody or fragment thereof is a padlock probe. In some embodiments, the nucleic acid probe comprises one or more nucleotide triphosphate analogs comprising functional moieties for immobilization. In some embodiments, the generated amplification product can be functionalized during the amplification, such as by adding nucleotide triphosphate analogs comprising functional moieties for immobilization. The tethering molecule can comprise a nucleic acid sequence complementary to the nucleic acid barcode. In some cases, the analyte is a nucleic acid molecule, and the tethering molecule can comprise a primer sequence complementary to a sequence of the nucleic acid molecule. The primer sequence can be hybridized to the sequence of the nucleic acid molecule. The primer sequence hybridized to the sequence of the nucleic acid molecule can then be extended to generate an extension product attached to the 3D matrix. Primer extension can comprise reverse transcription or second strand synthesis.

In some cases, a probe can be hybridized to the extension product. The hybridization can be performed in the presence of an additional hybridization reaction enhancing agent. The probe provided herein can be a padlock probe or a molecular inversion probe. The probe may be circularized. For example, the probe may be circularized by ligating the 3' end and the 5' end of the probe. The probe may be amplified to generate an amplification product. Various amplification methods can be used to amplify the probe, for example polymerase chain reaction or isothermal amplification. The amplification reaction can be rolling circle amplification. The amplification reaction can incorporate a modified base to the amplification product. The modified base can attach the amplification product to the 3D matrix. The modified base can be 5-azidomehtyl-dUTP. The amplification reaction can be a non-enzymatic reaction. Examples of non-enzymatic reaction include, but are not limited to, hybridization chain reaction (HCR) and branched DNA reaction. When performing the HCR, the probe may further comprise an initiator sequence, which can trigger a hybridization chain reaction of nucleic acid molecules from a pool of stable or metastable monomers (e.g., HCR monomers). The HCR monomers can adopt a hairpin structure. The HCR monomers can be directly or indirectly linked to detectable moieties. HCR can be used to amplify signal by increasing the number of detectable moieties, such as fluorophores, localized to the initiator sequence. When performing the branched DNA reaction, the probe may further comprise a sequence that can hybridize with a sequence of a pre-amplifier molecule. The pre-amplifier molecule can further comprise a sequence that is not hybridizable with the probe and can bind a plurality of nucleic acid molecules (e.g., branched DNA reaction monomers) to amplify a signal for detection.

In some cases, the analyte of the sample is a protein or a polypeptide. The protein or polypeptide can be a soluble protein, insoluble protein, surface cell receptor, ribonucleoprotein complex, or other peptide composition described herein. In some embodiments, the tethering molecule is an antibody or fragment thereof conjugated to a nucleic acid or nucleic acid barcode. In some embodiments, the tethering molecule is configured to hybridize to a nucleic acid or nucleic acid barcode conjugated to an antibody or fragment thereof for binding the analyte. The barcode may comprise one or more modified nucleotides with tethering functional groups, such as an azide group or other tethering moiety described herein. The sample may be embedded in a 3D matrix. The 3D matrix may be comprised of attachment moieties. The attachment moieties may comprise alkyl groups or other attachment moieties described herein. The attachment moieties may be covalently bound to the tethering moieties by click chemistry, free-radicals, or other attachment chemistry described herein. In one embodiment, a nucleic acid conjugated antibody or fragment thereof binds to a polypeptide analyte, the tethering moiety of the nucleic acid conjugated to the antibody or fragment thereof is covalently bound or linked to an attachment moiety of the 3D matrix, a protease or other protein clearing agent may be applied, and the nucleic acid conjugated to the antibody is detected by any method described herein.

In some embodiments, a combination of the tethering molecules described herein can be contacted or flowed through the matrix to detect multiple different analytes simultaneously or sequentially in the same tissue section, cell, or other sample. Nucleic acid probes, probed extension products, and nucleic acid barcoded antibodies may be used in combination to detect multiple analytes including nucleic acids, proteins, small molecules, or other analytes described herein, simultaneously or sequentially. In some cases, the combinations of tethering molecules and analytes can provide multiomic information, including various levels, expressions, or concentrations of multiple analytes, including those across different analyte types described herein.

Multiomic information may be generated by the detection of any combination of nucleic acids, including DNA and RNA, proteins or polypeptides, small molecules, lipids, or sugar moieties. In some cases, the multiomic information is generated from detecting signals associated with more than one nucleic acid, protein, polypeptide, small molecule, lipid, sugar moiety, or a combination thereof. In an example, multiomic information may be generated by detecting signals associated with a protein and an RNA. To generate protein and RNA multiomic information, a sample as described herein may be embedded in a 3D matrix as described herein comprising attachment moieties, an RNA-analyte binding probe comprising a tethering moiety and a protein-analyte binding agent (e.g., antibody) comprising a tethering moiety are flowed into the matrix, the RNA-analyte binding probe comprising a tethering moiety binds to an RNA, the protein-analyte binding agent or antibody comprising a tethering moiety binds to a protein, a click reaction mix is provided to the matrix and covalently bonds all tethering moieties to the attachment moieties of the 3D matrix, and the probes or antibodies are detected by any method described herein. In some other embodiments, the protein-analyte binding agent or antibody comprises a tethering moiety that is different from the tethering moiety of the RNA-analyte binding agent. In some embodiments, tethering of the protein-analyte (e.g., via the binding agent or antibody comprises a tethering moiety, using the nucleic acid barcode conjugated to the binding agent) to the attachment moieties of the 3D matrix is performed separately from tethering of the RNA-analyte to the attachment moieties of the 3D matrix. In some aspects, tethering molecules associated with a plurality of RNA analytes (or derivatives thereof) and tethering molecules associated with a plurality of protein analytes (or derivatives thereof) can be tethered directly or indirectly to attachment moieties of the 3D matrix. In some of any such embodiments, the tethering molecule can be provided before, during, and/or after the formation of the 3D matrix. In some of any such embodiments, the tethering molecule can attach to the attachment moieties during or after the formation of the 3D matrix. Any combination of nucleic acid, protein, polypeptide, small molecule, lipid, or sugar moiety binding agent or antibodies comprising of tethering moieties, or other tethering moiety molecules, may be used to generate multiomic information. Interrogation of multiple analytes can occur simultaneously or sequentially. Moreover, detection strategies for different types of analytes, including those described herein for nucleic acids and polypeptides and proteins, can be employed for multiomic analyses.

In some cases, the additional hybridization reaction enhancing agent can be inactivated or removed from the 3D matrix. In some embodiments, the additional hybridization reaction enhancing agent is removed, inactivated, or both, by washing. Examples of hybridization reaction enhancing agents are described elsewhere herein, with additional non-limiting examples described in PCT Publication No. WO2018/045181, U.S. Patent Publication No. 2019/

0177718, and U.S. Patent Publication No. 2019/0330617. Such hybridization reaction enhancing agents can be removed from a 3D matrix, including via washing.

The sample provided herein can be a biological sample. The biological sample can be a cell or a tissue. The cell or tissue can be fixed. The cell or tissue can be permeabilized. The cell or tissue can be fixed and then permeabilized.

FIG. 1 shows an example procedure of the methods provided herein. In a first operation 101, a container comprising a biological sample comprising an analyte within a synthetic three-dimensional (3D) matrix is provided. The synthetic 3D matrix can comprise an attachment moiety. Next, in a second operation 102, a tethering molecule is directed into the biological sample such that the tethering molecule can flow through the synthetic 3D matrix and come in contact with the analyte and attach to the analyte and the attachment moiety, thereby attaching the analyte to the synthetic 3D matrix.

In some aspects, the method for processing a biological sample can comprise contacting the biological sample comprising an analyte with a tethering molecule and a hybridization reaction enhancing agent. The tethering molecule can comprise a tethering moiety and a nucleic acid sequence complementary to a sequence of the analyte. The hybridization reaction enhancing agent can enhance a rate of hybridization between the nucleic acid sequence and the sequence of the analyte. Next, the nucleic acid sequence of the tethering molecule can be hybridized to the sequence of the analyte. Next, the biological sample having the tethering molecule hybridized to the analyte can be contacted with a matrix-forming material. Next, the matrix-forming material can be used to form a synthetic three-dimensional (3D) matrix with the tethering molecule attached thereto via the tethering moiety. The synthetic 3D matrix can preserve an absolute or relative spatial position of the analyte within the biological sample. The synthetic 3D matrix can further comprise an attachment moiety. The tethering moiety of the tethering molecule can have specificity for the attachment moiety. In some cases, the tethering moiety can be attached to the attachment moiety.

FIG. 2 shows an example procedure of the methods provided herein. In a first operation 201, a biological sample comprising an analyte is contacted with a tethering molecule and a hybridization reaction enhancing agent. The tethering molecule can comprise a tethering moiety and a nucleic acid sequence complementary to a sequence of the analyte. In a second operation 202, the nucleic acid sequence of the tethering molecule can be hybridized to the sequence of the analyte. In a third operation 203, the biological sample having the tethering molecule hybridized to the analyte is contacted with a matrix-forming material. In a fourth operation 204, the matrix-forming material is used to form a synthetic three-dimension (3D) matrix with the tethering molecule attached thereto via the tethering moiety.

Analytes

Provided herein are methods and systems for sample processing for use in analyte analysis or detection. The analyte may be a target of interest in a biological sample. In some cases, the analyte may be a nucleic acid molecule. In some cases, the analyte may be a protein. In the cases where the analyte is a protein, a binding agent which binds to the protein can be linked to a nucleic acid sequence which can then be detected by the methods and systems provided herein. For example, the binding agent can be an antibody or antibody fragment. The binding agent can be conjugated with a nucleic acid barcode. In some cases, the nucleic acid barcode can comprise a tethering moiety, which can link the nucleic acid barcode to the 3D matrix. In such cases, the binding agent may itself function as a tethering molecule. In some cases, the nucleic acid barcode can be linked to the 3D matrix through a tethering molecule comprising a nucleic acid sequence complementary to the nucleic acid barcode and a tethering moiety for attaching to the 3D matrix. The nucleic acid analyte can be a ribonucleic acid (RNA) or a deoxyribonucleic acid (DNA). The nucleic acid analyte may be naturally occurring nucleic acids or non-naturally occurring nucleic acids, such as nucleic acids that have been made using synthetic methods.

The nucleic acid targets, whether naturally occurring or synthetic, can be present within a three-dimensional (3D) matrix and covalently attached to the 3D matrix such that the relative position of each nucleic acid is fixed (e.g., immobilized) within the 3D matrix. In this manner, a 3D matrix of covalently bound nucleic acids of any sequence can be provided. Each nucleic acid may have its own three-dimensional coordinates within the matrix material and each nucleic acid may represent information. In this manner, a large amount of information can be stored in a 3D matrix. Individual information-encoding nucleic acid target, such as DNA or RNA can be amplified and sequenced in situ (i.e., within the matrix), thereby enabling a large amount of information to be stored and read in a suitable 3D matrix. Naturally occurring nucleic acid targets can include endogenous DNAs and RNAs. Synthetic nucleic acid targets can include primers, barcodes, amplification products and probes. The synthetic nucleic acid targets may be derived from the endogenous nucleic acid molecules or include sequence information of the endogenous nucleic acid molecules. The synthetic nucleic acid targets can be used to capture endogenous nucleic acid targets to the 3D matrix and can be subsequently sequenced or detected to identity the sequence information, positional (or spatial) information, or both, of the endogenous nucleic acid molecules. For example, a synthetic nucleic acid target can be a primer having a poly-deoxythymine (dT) sequence, which can hybridize to an endogenous mRNA molecule. The primer may be immobilized to the 3D matrix and may be extended to include sequence information (e.g., a sequence) of the mRNA molecule. The extended primer can then be captured by padlock probes and amplified in situ for detection. In another example, a synthetic nucleic acid target can be a barcode conjugated on an antibody. The barcode may be captured by padlock probes and amplified in situ for detection.

The nucleic acid target can be an endogenous nucleic acid in a biological sample, for example, genomic DNA, messenger RNA (mRNA), ribosomal RNA (rRNA), transfer RNA (tRNA), microRNA (miRNA), small cytoplasmic RNA (scRNA), and small nuclear RNA (snRNA). The nucleic acid target may be a synthetic nucleic acid linked to a binding agent. The binding agent may bind to any biological molecules to be detected in a biological sample. For example, to detect a protein, the binding agent may be an antibody or a portion thereof having a nucleic acid sequence linked thereto. For another example, to detect a protein, the binding agent may be an aptamer.

The nucleic acid target may be amplified to produce amplification products or amplicons within the 3D matrix. The nucleic acid target may be amplified using nucleic acid amplification, such as, for example, polymerase chain reaction (PCR). The nucleic acid target may be bound to a probe and the probe may be subsequently amplified to produce amplification products or amplicons. In some cases, the nucleic acid target is an RNA target, and the RNA target may be reverse transcribed to generate a cDNA. The cDNA may then be subjected to amplification or may be contacted with a probe (e.g., a padlock probe). The probe can hybridize with the cDNA. In some cases, the nucleic acid target is a DNA target, and the DNA target can be subjected to amplification or can be contacted with a probe (e.g., a padlock probe). For example, the DNA target can be amplified directly by an amplification primer. For another example, a padlock probe may be contacted with the DNA target and hybridize to the DNA target. The padlock probe can then be circularized and amplified. The amplification products or amplicons can be attached to the matrix, for example, by copolymerization or cross-linking. This can result in a structurally stable and chemically stable 3D matrix of nucleic acids. The 3D matrix of nucleic acids may allow for prolonged information storage and read-out cycles. The nucleic acid/amplicon matrix may allow for high throughput sequencing of a wide-ranging array of samples in three dimensions.

Three-Dimensional Matrix

The present disclosure provides a three-dimensional (3D) matrix. The 3D matrix may comprise a plurality of nucleic acids. The 3D matrix may comprise a plurality of nucleic acids covalently or non-covalently attached thereto. The 3D matrix can be a gel matrix. The 3D matrix can be a hydrogel matrix. The 3D matrix can preserve an absolute or relative 3D position of the plurality of nucleic acid molecules.

In some cases, a matrix-forming material may be used to form the 3D matrix. The matrix-forming material may be polymerizable monomers or polymers, or cross-linkable polymers. The matrix-forming material may be polyacrylamide, acrylamide monomers, cellulose, alginate, polyamide, agarose, dextran, or polyethylene glycol. The matrix-forming materials can form a matrix by polymerization, crosslinking of the matrix-forming materials, or both, using methods specific for the matrix-forming materials and methods, reagents and conditions. The matrix-forming material may form a polymeric matrix. The matrix-forming material may form a polyelectrolyte gel. The matrix-forming material may form a hydrogel gel matrix.

The matrix-forming material may form a 3D matrix including the plurality of nucleic acids while maintaining the spatial relationship of the nucleic acids. In this aspect, the plurality of nucleic acids can be immobilized within the matrix material. The plurality of nucleic acids may be immobilized within the matrix material by co-polymerization of the nucleic acids with the matrix-forming material. The plurality of nucleic acids may also be immobilized within the matrix material by crosslinking of the nucleic acids to the matrix material or otherwise cross-linking with the matrix-forming material. The plurality of nucleic acids may also be immobilized within the matrix by covalent attachment or through ligand-protein interaction to the matrix.

The matrix can be porous thereby allowing the introduction of reagents into the matrix at the site of a nucleic acid for amplification of the nucleic acid. A porous matrix may be made according to various methods. For example, a polyacrylamide gel matrix can be co-polymerized with acrydite-modified streptavidin monomers and biotinylated DNA molecules, using a suitable acrylamide:bis-acrylamide ratio to control the cross-linking density. Additional control over the molecular sieve size and density can be achieved by adding additional cross-linkers such as functionalized polyethylene glycols.

The 3D matrix may be sufficiently optically transparent or may have optical properties suitable for standard sequencing chemistries and deep three-dimensional imaging for high throughput information readout. Examples of the sequencing chemistries that utilize fluorescence imaging include ABI SoLiD (Life Technologies), in which a sequencing primer on a template is ligated to a library of fluorescently labeled octamers with a cleavable terminator. After ligation, the template can then be imaged using four color channels (FITC, Cy3, Texas Red and Cy5). The terminator can then be cleaved off leaving a free-end to engage in the next ligation-extension cycle. After all dinucleotide combinations have been determined, the images can be mapped to the color code space to determine the specific base calls per template. The workflow can be achieved using an automated fluidics and imaging device (i.e., SoLiD 5500 W Genome Analyzer, ABI Life Technologies). Another example of sequencing platform uses sequencing by synthesis, in which a pool of single nucleotide with a cleavable terminator can be incorporated using DNA polymerase. After imaging, the terminator can be cleaved and the cycle can be repeated. The fluorescence images can then be analyzed to call bases for each DNA amplicons within the flow cell (HiSeq, Illumina).

Biological Samples

A biological sample may be provided in the methods, systems and compositions described herein. The biological sample can comprise the analyte to be processed, detected, or both, using the methods described herein.

In some aspects, a biological sample may be fixed in the presence of the matrix-forming materials, for example, hydrogel subunits. By "fixing" the biological sample, it is meant exposing the biological sample, e.g., cells or tissues, to a fixation agent such that the cellular components become crosslinked to one another. By "hydrogel" or "hydrogel network" is meant a network of polymer chains that are water-insoluble, sometimes found as a colloidal gel in which water is the dispersion medium. In other words, hydrogels are a class of polymeric materials that can absorb large amounts of water without dissolving. Hydrogels can contain over 99% water and may comprise natural or synthetic polymers, or a combination thereof. Hydrogels may also possess a degree of flexibility very similar to natural tissue, due to their significant water content. By "hydrogel subunits" or "hydrogel precursors" refers to hydrophilic monomers, prepolymers, or polymers that can be crosslinked, or "polymerized", to form a 3D hydrogel network. Without being bound by any scientific theory, fixation of the biological sample in the presence of hydrogel subunits may crosslink the components of the biological sample to the hydrogel subunits, thereby securing molecular components in place, preserving the tissue architecture and cell morphology.

In some cases, the biological sample (e.g., cell or tissue) may be permeabilized or otherwise made accessible to an environment external to the biological sample. In some cases, the biological sample may be fixed and permeabilized first, and then a matrix-forming material can then be added into the biological sample.

Any suitable biological sample that comprises nucleic acid may be obtained from a subject. Any suitable biological sample that comprises nucleic acid may be used in the methods and systems described herein. A biological sample may be solid matter (e.g., biological tissue) or may be a fluid (e.g., a biological fluid). In general, a biological fluid can include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, micropiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, other excretions or body tissues, or a combination thereof. A biological sample may be a cell-free sample. Such cell-free sample may include DNA and/or RNA.

Any convenient fixation agent, or "fixative," may be used to fix the biological sample in the absence or in the presence of hydrogel subunits, for example, formaldehyde, paraformaldehyde, glutaraldehyde, acetone, ethanol, methanol, etc. In some cases, the fixative may be diluted in a buffer, e.g., saline, phosphate buffer (PB), phosphate buffered saline (PBS), citric acid buffer, potassium phosphate buffer, etc., usually at a concentration of about 1-10%, e.g. 1%, 2%, 3%, 4%, 5%, 6%, 7%, 8%, or 10%, for example, 4% paraformaldehyde/0.1M phosphate buffer; 2% paraformaldehyde/ 0.2% picric acid/0.1M phosphate buffer; 4% paraformaldehyde/0.2% periodate/1.2% lysine in 0.1 M phosphate buffer; 4% paraformaldehyde/0.05% glutaraldehyde in phosphate buffer; etc. The type of fixative used and the duration of exposure to the fixative will depend on the sensitivity of the molecules of interest in the specimen to denaturation by the fixative and may be readily determined using histochemical or immunohistochemical techniques.

The fixative/hydrogel composition may comprise any hydrogel subunits, such as, but not limited to, poly(ethylene glycol) and derivatives thereof (e.g. PEG-diacrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly (hydroxyethyl methacrylate), collagen, hyaluronic acid, chitosan, dextran, agarose, gelatin, alginate, protein polymers, methylcellulose and the like. Agents such as hydrophilic nanoparticles, e.g., poly-lactic acid (PLA), poly-glycolic acid (PLG), poly(lactic-co-glycolic acid) (PLGA), polystyrene, poly(dimethylsiloxane) (PDMS), etc. may be used to improve the permeability of the hydrogel while maintaining patternability. Materials such as block copolymers of PEG, degradable PEO, poly(lactic acid) (PLA), and other similar materials can be used to add specific properties to the hydrogel. Crosslinkers (e.g. bis-acrylamide, diazirine, etc.) and initiators (e.g. azobisisobutyronitrile (AIBN), riboflavin, L-arginine, etc.) may be included to promote covalent bonding between interacting macromolecules in later polymerization events.

The biological sample (e.g., a cell or tissue) may be permeabilized after being fixed. Permeabilization may be performed to facilitate access to cellular cytoplasm or intracellular molecules, components or structures of a cell. Permeabilization may allow an agent (such as a phosphoselective antibody, a nucleic acid conjugated antibody, a nucleic acid probe, a primer, etc.) to enter into a cell and reach a concentration within the cell that is greater than that which can normally penetrate into the cell in the absence of such permeabilizing treatment. In some embodiments, cells may be stored following permeabilization. In some cases, the cells may be contacted with one or more agents to allow penetration of the one or more agent after permeabilization without any storage step and then analyzed. In some embodiments, cells may be permeabilized in the presence of at least about 60%, 70%, 80%, 90% or more methanol (or ethanol) and incubated on ice for a period of time. The period of time for incubation can be at least about 10, 15, 20, 25, 30, 35, 40, 50, 60 or more minutes.

In some embodiments, permeabilization of the cells may be performed by any suitable method. Selection of an appropriate permeabilizing agent and optimization of the incubation conditions and time may be performed. Suitable methods include, but are not limited to, exposure to a detergent (such as CHAPS, cholic acid, deoxycholic acid, digitonin, n-dodecyl-beta-D-maltoside, lauryl sulfate, gly-codeoxycholic acid, n-lauroylsarcosine, saponin, and triton X-100) or to an organic alcohol (such as methanol and ethanol). Other permeabilizing methods can comprise the use of certain peptides or toxins that render membranes permeable. Permeabilization may also be performed by addition of an organic alcohol to the cells.

Permeabilization can also be achieved, for example, by way of illustration and not limitation, through the use of surfactants, detergents, phospholipids, phospholipid binding proteins, enzymes, viral membrane fusion proteins and the like; through the use of osmotically active agents; by using chemical crosslinking agents; by physicochemical methods including electroporation and the like, or by other permeabilizing methodologies.

Thus, for instance, cells may be permeabilized using any of a variety of known techniques, such as exposure to one or more detergents (e.g., digitonin, Triton X-100™, NP-40™, octyl glucoside and the like) at concentrations below those used to lyse cells and solubilize membranes (i.e., below the critical micelle concentration). Certain transfection reagents, such as dioleoyl-3-trimethylammonium propane (DOTAP), may also be used. ATP can also be used to permeabilize intact cells. Low concentrations of chemicals used as fixatives (e.g., formaldehyde) may also be used to permeabilize intact cells.

The biological sample within the 3D matrix may be cleared of proteins, lipids, or both, that are not targets of interest. The biological sample within the 3D matrix may be treated with a clearing agent after a nucleic acid that can be associated with an analyte (e.g., protein) is bound via a tethering moiety to the 3D matrix. For example, the biological sample can be cleared of proteins (also called "deproteination") by enzymatic proteolysis. The clearing process may be performed before or after covalent immobilization of any target molecules or derivatives thereof.

In some cases, the clearing process is performed after covalent immobilization of target nucleic acid molecules (e.g., RNA or DNA), primers (e.g., RT primers), derivatives of target molecules (e.g., cDNA or amplicons), probes (e.g., padlock probes) to a synthetic 3D matrix. Performing the clearing process after immobilization can enable any subsequent nucleic acid hybridization reactions to be performed under conditions where the sample has been substantially deproteinated, as by enzymatic proteolysis ("protein clearing"). This method can have the benefit of removing ribosomes and other RNA- or nucleic-acid-target-binding proteins from the target molecule (while maintaining spatial location), where the protein component may impede or inhibit primer binding, reverse transcription, or padlock ligation and amplification, thereby improving the sensitivity and quantitativity of the assay by reducing bias in probe capture events due to protein occupation of or protein crowding/proximity to the target nucleic acid.

The clearing process can comprise removing non-targets from the 3D matrix. The clearing process can comprise degrading the non-targets. The clearing process can comprise exposing the sample to an enzyme (e.g., a protease) able to degrade a protein. The clearing process can comprise exposing the sample to a detergent.

Proteins may be cleared from the sample using enzymes, denaturants, chelating agents, chemical agents, and the like, which may break down the proteins into smaller components and/or amino acids. These smaller components may be easier to remove physically, may be sufficiently small or inert such that they do not significantly affect the background, or both. Similarly, lipids may be cleared from the sample using surfactants or the like. In some cases, one or more of these agents are used, e.g., simultaneously or sequentially. Non-limiting examples of suitable enzymes include proteinases such as proteinase K, proteases or peptidases, or digestive enzymes such as trypsin, pepsin, or chymotrypsin. Non-limiting examples of suitable denaturants include guanidine HCl, acetone, acetic acid, urea, or lithium perchlorate. Non-limiting examples of chemical agents able to denature proteins include solvents such as phenol, chloroform, guanidinium isocyananate, urea, formamide, etc. Non-limiting examples of surfactants include Triton X-100 (polyethylene glycol p-(1,1,3,3-tetramethylbutyl)-phenyl ether), SDS (sodium dodecyl sulfate), Igepal CA-630, or poloxamers. Non-limiting examples of chelating agents include ethylenediaminetetraacetic acid (EDTA), citrate, or polyaspartic acid. In some embodiments, compounds such as these may be applied to the sample to clear proteins, lipids, other components, or both. For instance, a buffer solution (e.g., containing Tris or tris(hydroxymethyl)aminomethane) may be applied to the sample, then removed.

In some cases, nucleic acids that are not target of interest may also be cleared. These non-target nucleic acids may not be captured, immobilized to the 3D matrix, or both, and therefore can be removed with an enzyme to degrade nucleic acid molecules. Non-limiting examples of DNA enzymes that may be used to remove DNA include DNase I, dsDNase, a variety of restriction enzymes, etc. Non-limiting examples of techniques to clear RNA include RNA enzymes such as RNase A, RNase T, or RNase H, or chemical agents, e.g., via alkaline hydrolysis (for example, by increasing the pH to greater than 10). Non-limiting examples of systems to remove sugars or extracellular matrix include enzymes such as chitinase, heparinases, or other glycosylases. Non-limiting examples of systems to remove lipids include enzymes such as lipidases, chemical agents such as alcohols (e.g., methanol or ethanol), or detergents such as Triton X-100 or sodium dodecyl sulfate. In this way, the background of the sample may be removed, which may facilitate analysis of the nucleic acid probes or other targets, e.g., using fluorescence microscopy, or other techniques as described herein.

Immobilization to the Three-Dimensional Matrix

Provided herein are compositions and methods by which target analytes or derivatives can be tethered into a preexisting matrix, including without initiating a free-radical hydrogel polymerization reaction. A 3D matrix, such as a 3D hydrogel matrix, can comprise functional tethering moieties, which are reactive to compatible tethering moieties present on target analytes or derivatives or probes.

In various aspects of the present disclosure, a tethering molecule can be used to attach an analyte to the three-dimensional (3D) matrix. The tethering molecule can be a nucleic acid molecule having a sequence complementary to a sequence of the target nucleic acid molecule. In some cases, the tethering molecule can have a free 3' end that can be extended in a polymerization reaction. For example, the tethering molecule can be a primer or a nucleic acid probe. In some cases, the analyte is an RNA molecule and the tethering molecule is a padlock probe. The primer can be a reverse transcription (RT) primer targeting ribonucleic acid molecules. The primer can be a poly-dT primer. In some cases, the primer can be a padlock RT primer. In some cases where the analyte is a polypeptide molecule (e.g., a protein), the polypeptide molecule may be bound by a binding agent linked to a nucleic acid sequence, which can then be detected by the methods and systems provided herein. For example, the binding agent can be a nucleic acid barcode conjugated antibody or antibody fragment. The tethering molecule can have a sequence complementary to the nucleic acid barcode of the antibody or fragment thereof. In some cases, the binding agent comprising a nucleic acid barcode can itself function as a tethering molecule, which can be used to attach the binding agent to the 3D matrix directly. In such cases, the nucleic acid barcode may comprise a tethering moiety for attaching to the 3D matrix.

The tethering molecule can comprise a tethering moiety for attaching the tethering molecule to the 3D matrix. The 3D matrix can comprise an attachment moiety. The tethering moiety can bind to the attachment moiety such that the tethering molecule can be attached to the 3D matrix. The tethering moiety and the attachment moiety can be functional moieties that can react with each other. The tethering moiety and the attachment moiety can comprise click functional moieties that react with each other via click chemistry, such as Copper(I)-catalyzed Azide-Alkyne Cycloaddition (CuAAC) click chemistry. For example, the tethering moiety can comprise an alkyne, and the attachment moiety can be an azide, or vice versa. Attachment moieties may be in the form of monomers, polymers, or crosslinkers incorporated into a 3D matrix during 3D matrix formation (such as, for example, during free-radical polymerization), including acrylamide-co-alkyne (propargyl acrylamide), compounds with acryloyl groups or other moieties which participate in 3D matrix formation and are thereby incorporated into the 3D matrix. Attachment moieties can also be incorporated into a 3D matrix after 3D matrix formation. A monomer group may be polyethylene glycol (PEG) or another hydrogel or matrix component. The tethering moiety may comprise an azide, thiol, amine, alkyne, or other groups which can be used for the purpose of conjugation or bioconjugation. Some embodiments include tethering moieties or attachment moieties which are reactive under certain conditions and not under other conditions, such as those for which the conjugation reaction is catalyzed, such as the Copper(I)-catalyzed Azide-Alkyne Cycloaddition (CuAAC) copper-catalyzed click reaction. Other methods of catalyzing or gating the conjugation reaction include by temperature, pH, photo-reactive groups (including photo-catalyzed click reactions), or redox state, including reduction and oxidation of thiol groups and disulfide linkages. Such functionality enables a reagent, such as a probe, to be introduced into the 3D matrix or other matrix, to perfuse through and bind to a target analyte, such as by nucleic acid hybridization or antibody binding to proteins, or to participate in a reaction such as synthesis of a derivative molecule (cDNA, polony, rolony, etc.), and subsequently be linked to the 3D matrix via a tethering moiety. This can result in non-uniform spatial localization of the conjugated product, e.g. as localized to a target analyte. Examples of click functional moieties include, but are not limited to, an amine, a thiol, an azide, an alkyne, a nitrone, an alkene, a tetrazine, a tetrazole and an acrydite. As used herein, the term "reactive group" or "functional moiety" means any moiety on a first reactant that is capable of reacting chemically with another functional moiety or reactive group on a second reactant to form a covalent or ionic linkage. For example, a reactive group of the monomer or polymer of the matrix-forming material can react chemically with a functional moiety (or another reactive group) on the substrate of interest or the target to form a covalent or ionic linkage. The substrate of interest or the target may then be immobilized to the matrix via the linkage formed by the reactive group and the functional moiety. Examples of suitable reactive groups or functional moieties include electrophiles or nucleophiles that can form a covalent linkage by reaction with a corresponding nucleophile or electrophile, respectively, on the substrate of interest. Non-limiting examples of suitable electrophilic reactive groups may include, for example, esters including activated esters (such as, for example, succinimidyl esters), amides, acrylamides, acyl azides, acyl halides, acyl nitriles, aldehydes, ketones, alkyl halides, alkyl sulfonates, anhydrides, aryl halides, aziridines, boronates, carbodiimides, diazoalkanes, epoxides, haloacetamides, haloplatinates, halotriazines, imido esters, isocyanates, isothiocyanates, maleimides, phosphoramidites, silyl halides, sulfonate esters, sulfonyl halides, and the like. Non-limiting examples of suitable nucleophilic reactive groups may include, for example, amines, anilines, thiols, alcohols, phenols, hyrazines, hydroxylamines, carboxylic acids, glycols, heterocycles, and the like. The tethering moiety and the attachment moiety can be a binding pair, for example, protein-protein binding pair. The tethering moiety and the attachment moiety can form a non-covalent interaction, for example, an ionic interaction, a Van der Waals force, a hydrophobic interaction and a hydrogen bonding. The tethering moiety can be a biotin (or derivatives thereof), and the attachment moiety can be an avidin (e.g., a streptavidin), and vice versa.

In some cases, other nucleic acids (e.g., RNA molecule, cDNA molecule, primer, or probe) described herein may comprise a functional moiety. The nucleic acids can be linked to the 3D matrix by the functional moiety. The functional moiety can be reacted with a reactive group on the 3D matrix through conjugation chemistry. In some cases, the functional moiety can be attached to target of interest through conjugation chemistry. In some cases, the functional moiety can be directly attached to a reactive group on the native nucleic acid molecule. In some cases, the functional moiety can be indirectly linked to a target through an intermediate chemical or group. The conjugation strategies described herein are not limited to nucleic acid targets and can be used for protein or small molecule targets as well. A nucleotide analog comprising a functional moiety may be incorporated into a growing chain of the nucleic acid (e.g., cDNA molecule, probe, or primer) during nucleic acid synthesis or an extension reaction.

The cDNA molecule may be functionalized during the reverse transcription reaction, such as by adding nucleotide triphosphate analogs comprising functional moieties for immobilization. Such nucleotide triphosphate analogs include, but are not limited to, amino-allyl dUTP, 5-TCO-PEG4-dUTP, C8-Alkyne-dUTP, 5-Azidomethyl-dUTP, 5-Vinyl-dUTP, 5-Ethynyl dUTP, and other nucleotide triphosphate analogs comprising a functional moiety for cDNA immobilization by cross-linking, or forming a chemical bond between the cDNA and in situ matrix, cellular or synthetic. Furthermore, the in-situ matrix, cellular or synthetic, may contain or be made to contain chemical moieties (e.g., reactive groups) that can react with the functional moieties in the cDNA through functionalization reactions.

For example, amino-allyl dUTP may be cross-linked to endogenous free amine groups present in proteins and other biomolecules present within the endogenous or exogenous cellular matrix, or present in a modified synthetic hydrogel matrix, such as an amine-functionalized polyacrylamide hydrogel formed by copolymerization of polyacrylamide and N-(3-aminopropyl)-methacrylamide; likewise nucleoside analogs containing azide functional moieties may be cross-linked to a synthetic hydrogel matrix comprising alkyne functional moieties, such as that formed by copolymerization of acrylamide and propargyl acrylamide.

The cDNA molecule may be functionalized with moieties for immobilization subsequent to reverse transcription. Mechanisms for post-synthesis cDNA functionalization may include a variety of biochemical and chemical methods. These include, but are not limited to, use of a ligation reaction to conjugate an oligonucleotide bearing a functional moiety for immobilization to the cDNA molecule, use of a DNA polymerization reaction to add templated or un-templated bases to the cDNA, as in the process of A-tailing by Taq polymerize, or by using the reactions mediated by DNA end-repair mechanisms. Alternatively, a chemical method of DNA chemical functionalization may be used to conjugate functional moieties for immobilization. For example, Label-IT Amine and Label-X are bifunctional reagents that can react with nucleic acids via a nitrogen mustard alkylation mechanism for the purpose of conjugating free amine or acryloyl groups to the nucleic acid, which can be used for the purpose of immobilization to the matrix. Other chemistries, including but not limited to, DNA alkylation and oxymercuration, can provide mechanisms for functionalizing DNA.

The present disclosure provides a method of modifying one or more analytes (e.g., a nucleic acid and/or other macromolecules) in situ to comprise a functional moiety. In some cases, the functional moiety may comprise a polymerizable group. In some cases, the functional moiety may comprise a free radical polymerizable group. In some cases, the functional moiety may comprise an amine, a thiol, an azide, an alkyne, a nitrone, an alkene, a tetrazine, a tetrazole, an acrydite or other click reactive group. In some cases, the functional moiety can be subsequently linked to a 3D matrix in situ. The functional moiety may further be used to preserve the absolute or relative spatial relationships among two or more molecules within a sample.

In some embodiments, two or more conjugation reactions (e.g., copper-catalyzed click reactions) are performed during processing of a sample to attach two or more types of analytes (directly or indirectly) to the 3D matrix. In an exemplary workflow, the method comprises: contacting a biological sample comprising multiple types of analytes (e.g., nucleic acid analytes and polypeptide analytes) with a binding agent (e.g., an antibody or fragment thereof) conjugated to a nucleic acid barcode associated with a tethering moiety (e.g., acryloyl group); binding said polypeptide analyte with said binding agent; performing reverse transcription to generate cDNA from the nucleic acid analytes; forming a synthetic three-dimensional (3D) matrix and tethering the binding agent and/or associated nucleic acid barcode; treating the sample with a clearing agent; optionally releasing the generated cDNA; contacting the sample with a probe (or a probe set comprising other nucleic acid molecules such as a splint for hybridization and/or ligation), wherein the probe hybridizes to the one or more analytes; ligating the probe(s); performing an amplification reaction (e.g., RCA using the hybridized and ligated probe as template); tethering the amplification product to the 3D matrix (e.g., using functionalized moieties incorporated into the product during amplification, such as azide-dUTP); and analyzing the one or more analytes. In some cases, one or more of the aspects of the exemplary workflow can be performed in various orders and one or more additional aspects can be performed to process the sample and/or the analytes throughout the workflow.

Supports

A matrix may be used in conjunction with a support (e.g., a solid or semi-solid support). For example, the matrix can be polymerized in such a way that one surface of the matrix is attached to a support (e.g., a glass surface, a flow cell, a glass slide, a well), while the other surface of the matrix is exposed or sandwiched between two solid supports. According to one aspect, the matrix can be contained within a container. In some cases, the biological sample may be fixed or immobilized on a support.

The support of the present disclosure may be fashioned into a variety of shapes. In certain embodiments, the support is substantially planar. Examples of support include plates such as slides, multiwell plates, flow cells, coverslips, microchips, and the like, containers such as microfuge tubes, test tubes and the like, tubing, sheets, pads, films and the like. Additionally, the support may be, for example, biological, non-biological, organic, inorganic, or a combination thereof.

As used herein, the term "solid surface" is intended to mean the surface of a solid or semi-solid support and includes any material that can serve as a solid or semi-solid foundation for attachment of a biological sample or other molecules such as polynucleotides, amplicons, DNA balls, other nucleic acids, other polymers, including biopolymers, or a combination thereof. Example types of materials comprising solid surfaces include glass, modified glass, functionalized glass, inorganic glasses, microspheres, including inert particles, magnetic particles, both inert and magnetic particles, plastics, polysaccharides, nylon, nitrocellulose, ceramics, resins, silica, silica-based materials, carbon, metals, an optical fiber or optical fiber bundles, a variety of polymers other than those described above and multiwell plates. Example types of plastics include, but are not limited to, acrylics, polystyrene, copolymers of styrene and other materials, polypropylene, polyethylene, polybutylene, polyurethanes and Teflon™. Example types of silica-based materials include, but are not limited to, silicon and various forms of modified silicon.

Solid surfaces can also be varied in their shape depending on the application in a method described herein. For example, a solid surface useful in the present disclosure can be planar or contain regions which are concave or convex.

Amplifications

Any type of nucleic acid amplification reaction may be used to perform an amplification reaction in the methods or systems described herein and generate an amplification product. Moreover, amplification of a nucleic acid may be linear, exponential, or a combination thereof. Non-limiting examples of nucleic acid amplification methods include transcription (e.g., in vitro transcription), reverse transcription, primer extension, polymerase chain reaction, ligase chain reaction, helicase-dependent amplification, asymmetric amplification, rolling circle amplification, and multiple displacement amplification (MDA). In some cases, the amplified product may be DNA. In cases where a target RNA is amplified, DNA can be obtained by reverse transcription of the RNA and subsequent amplification of the DNA can be used to generate an amplified DNA product. In some cases, a target RNA is reverse transcribed by a reverse transcriptase to generate a cDNA. In some cases, a target DNA is transcribed by an RNA polymerase to generate an RNA. The amplified DNA product may be indicative of the presence of the target RNA in the biological sample. In cases where DNA is amplified, any DNA amplification method may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touch-down PCR), and ligase chain reaction (LCR). In some cases, DNA amplification is linear. In some cases, DNA amplification is exponential. In some cases, DNA amplification is achieved with nested PCR, which can improve sensitivity of detecting amplified DNA products.

The amplification of nucleic acid sequences may be performed within the matrix. Methods of amplifying nucleic acids may include rolling circle amplification in situ. In certain aspects, methods of amplifying nucleic acids may include the use of PCR, such as anchor PCR, RACE PCR, or a ligation chain reaction (LCR). Alternative amplification methods include but are not limited to self-sustained sequence replication, transcriptional amplification system, Q-Beta Replicase, recursive PCR or any other nucleic acid amplification method.

The nucleic acids within the 3D matrix may be contacted with reagents under suitable reaction conditions sufficient to amplify the nucleic acids. The matrix may be porous to allow migration of reagents into the matrix to contact the nucleic acids. In certain aspects, nucleic acids may be amplified by selectively hybridizing an amplification primer to an amplification site at the 3' end of a nucleic acid sequence. Amplification primers are 6 to 100, and even up to 1,000, nucleotides in length, but sometimes from 10 to 40 nucleotides, although oligonucleotides of different length are of use. In some cases, the amplification primer can be at least about 5, 6, 7, 8, 9, 10, 11, 12, 13, 14, 15, 16, 17, 18, 19, 20, 21, 22, 23, 24, 25, or more nucleotides in length. In some cases, the amplification primer can be at least about 20, 30, 40, 50, 60, 70, 80, 90, 100, 200, 300, 400, 500, or more nucleotides in length. Amplification primers may hybridize to a nucleic acid probe that hybridizes to a DNA molecule such that the amplification primers can be used to amplify a sequence of the nucleic acid probe. Amplification primers may be present in solution to be added to the matrix or they may be added during formation of the matrix to be present therein sufficiently adjacent to nucleic acids to allow for hybridization and amplification.

A DNA polymerase can be used in an amplification reaction. Any suitable DNA polymerase may be used, including commercially available DNA polymerases. A DNA polymerase generally refers to an enzyme that is capable of incorporating nucleotides to a strand of DNA in a template bound fashion. Non-limiting examples of DNA polymerases include Taq polymerase, Tth polymerase, Tli polymerase, Pfu polymerase, VENT polymerase, DEEP-VENT polymerase, EX-Taq polymerase, LA-Taq polymerase, Expand polymerases, Sso polymerase, Poc polymerase, Pab polymerase, Mth polymerase, Pho polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, and variants, modified products and derivatives thereof. Other enzymes can also be used for an amplification reaction, including but not limited to, an RNA polymerase (e.g., T7 RNA polymerase, SP6 RNA polymerase, T3 RNA polymerase, etc.) and a reverse transcriptase (e.g., Avian myeloblastosis virus (AMV) reverse transcriptase, a wild type human immunodeficiency virus-1 (HIV-1) reverse transcriptase, or a Moloney Murine Leukemia Virus (M-MLV) reverse transcriptase).

Detections

The present disclosure provides methods and systems for sample processing for use in nucleic acid detection. A sequence of the nucleic acid target may be identified. Various methods can be used for nucleic acid detection, including hybridization and sequencing. Nucleic acid detection can comprise imaging the biological sample or the 3D matrix described herein.

Reporter agents may be linked with nucleic acids, including amplified products, by covalent or non-covalent interactions. Non-limiting examples of non-covalent interactions include ionic interactions, Van der Waals forces, hydrophobic interactions, hydrogen bonding, and combinations thereof. Reporter agents may bind to initial reactants and changes in reporter agent levels may be used to detect amplified product. Reporter agents may be detectable (or non-detectable) as nucleic acid amplification progresses. Reporter agents may be optically detectable. An optically-active dye (e.g., a fluorescent dye) may be used as a reporter agent. Non-limiting examples of dyes include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 or 6-carboxy fluorescein (FAM), 5,6-carboxy fluorescein (FAM), 5-(or 6-) iodoacetamidofluorescein, 5-{[2 (and 3)-5-(Acetylmercapto)-succinyl] amino}fluorescein (SAMSA-fluorescein), lissamine rhodamine B sulfonyl chloride, 5 or 6 carboxy rhodamine (ROX), 5,6 carboxy rhodamine (ROX), 7-amino-methylcoumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

In some embodiments, a reporter agent may be a sequence-specific oligonucleotide probe that is optically active when hybridized with a nucleic acid target or derivative thereof (e.g., an amplified product). A probe may be linked to any of the optically-active reporter agents (e.g., dyes) described herein and may also include a quencher capable of blocking the optical activity of an associated dye. Non-limiting examples of probes that may be useful used as reporter agents include TaqMan probes, TaqMan Tamara probes, TaqMan MGB probes, or Lion probes.

In some aspects, the method for determining the nucleic acid sequence of a target nucleic acid molecule includes sequencing or sequence analysis. In some aspects, sequencing by synthesis, sequencing by ligation or sequencing by hybridization is used for determining the nucleic acid sequence of a target nucleic acid molecule. As disclosed herein, various amplification methods can be employed to generate larger quantities, particularly of limited nucleic acid samples, prior to sequencing. For example, the amplification methods can produce a targeted library of amplicons.

For sequencing by ligation, labeled nucleic acid fragments may be hybridized and identified to determine the sequence of a target nucleic acid molecule. For sequencing by synthesis (SBS), labeled nucleotides can be used to determine the sequence of a target nucleic acid molecule. A target nucleic acid molecule can be hybridized with a primer and incubated in the presence of a polymerase and a labeled nucleotide containing a blocking group. The primer can be extended such that the labeled nucleotide is incorporated. The presence of the blocking group may permit the incorporation of a single nucleotide. The presence of the label can permit identification of the incorporated nucleotide. As used herein, a label can be any optically active dye described herein. Either single bases can be added or, alternatively, all four bases can be added simultaneously, particularly when each base is associated with a distinguishable label. After identifying the incorporated nucleotide by its corresponding label, both the label and the blocking group can be removed, thereby allowing a subsequent round of incorporation and identification. Thus, cleavable linkers can link the label to the base. Examples of cleavable linker include, but are not limited to, peptide linkers. Additionally, a removable blocking group may be used so that multiple rounds of identification can be performed, thereby permitting identification of at least a portion of the target nucleic acid sequence. The compositions and methods disclosed herein are useful for such an SBS approach. In addition, the compositions and methods can be useful for sequencing from a solid support (e.g., an array or a sample within a 3D matrix as described herein), where multiple sequences can be "read" simultaneously from multiple positions on the solid support since each nucleotide at each position can be identified based on its identifiable label. Example methods are described in US 2009/0088327; US 2010/0028885; and US 2009/0325172, each of which is incorporated herein by reference.

Computer Systems

The present disclosure provides computer systems that are programmed to implement methods of the disclosure. FIG. 3 shows a computer system 301 that is programmed or otherwise configured to process a sample using the methods of the present disclosure. The computer system 301 can regulate various aspects of sample processing of the present disclosure, such as, for example, providing a sample in a sample holder, contacting a reagent or buffer to the sample, performing a reaction within the sample and sequencing. The computer system 301 can be an electronic device of a user or a computer system that is remotely located with respect to the electronic device. The electronic device can be a mobile electronic device.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user (e.g., a user performing sample processing or nucleic acid sequence detection of the present disclosure). Examples of remote computer systems include personal computers (e.g., portable PC), slate or tablet PC's (e.g., Apple® iPad, Samsung®

Galaxy Tab), telephones, Smart phones (e.g., Apple® iPhone, Android-enabled device, Blackberry®), or personal digital assistants. The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340 for providing, for example, protocols to perform the sample processing methods and/or nucleic acid sequence detection methods described in the present disclosure. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 305. The algorithm can, for example, be executed so as to process a sample and/or detect a nucleic acid sequence utilizing methods and systems disclosed in the present disclosure.

EXAMPLE

Example 1—Analyte Immobilization in a
Three-Dimensional Matrix Protocol 1

The example provides a protocol for processing a sample for detection within a three-dimensional (3D) matrix. The protocol can comprise (1) permeabilizing a sample and embedding the sample with a click-gel (e.g., gel matrix having attachment moieties to attach targets of interest); (2) hybridizing tethering oligos (e.g., plurality of padlock RT primers with 5' tethering moiety or poly(dT) primer with tethering moiety) with a crowding agent (e.g., a hybridization reaction enhancing agent); (3) linking the tethering oligos to the gel via CuAAC click chemistry; (4) inactivating or washing out the crowding agent and treating the sample with protease to clear the sample and fully permeabilize the sample; (5) performing reverse transcription of the hybridized RT primers; (6) hybridizing padlock probes in the presence of a crowding agent; (7) inactivating or washing out the crowding agent; (8) circularizing the padlock probes by ligation and performing rolling circle amplification (RCA) to incorporate 5-azidomethyl-dUTP; and (9) attaching rolonies to gel matrix by click chemistry.

Example 2—Analyte Immobilization in a
Three-Dimensional Matrix Protocol 2

The example provides a protocol for processing a sample for detection within a three-dimensional (3D) matrix. The protocol can comprise (1) permeabilizing a sample and hybridizing tethering oligos (e.g., plurality of padlock RT primers with 5' tethering moiety or poly(dT) probe with tethering moiety) in the presence of a crowding agent; (2) embedding the tethering oligos and the sample in a gel matrix to tether 5' acrydite group of the tethering oligos to the gel matrix; (3) inactivating or washing out the crowding agent and treating the sample with a protease to clear the sample and fully permeabilize the sample; (4) subjecting the sample to reverse transcription to extend the hybridized RT primers; (5) hybridizing the padlock probes in the presence of a crowding agent; (6) inactivating or washing out the crowding agent; (7) circularizing the padlock probes by ligation and performing rolling circle amplification (RCA) to incorporate 5-azidomethyl-dUTP; and (8) attaching rolonies to the gel matrix.

Example 3—Analyte Tethering Using Reverse Transcriptase

The example provides a protocol for tethering analytes of a sample to a three-dimensional matrix via reverse transcriptase polymerization of modified nucleotides comprising functional tethering moieties. The protocol can comprise (1) permeabilizing a tissue section sample; (2) embedding the tissue section sample in a 3D matrix with 4% w/v 19:1 acrylamide:bisacrylamide with additional 0.1% propargyl acrylamide using APS/TEMED; (3) introducing a reverse transcription reaction mix including reverse transcriptase and RT primer, such as random (N)x6, (N)x8, etc., or Poly(dT), bearing a 5' azide modification tethering moiety; (4) washing the sample (5) adding a click reaction mix comprising copper salt and sodium ascorbate, which catalyzes linkage between the generated cDNA and matrix; (6) hybridizing padlock probes and ligating the probes to form circular templates; (7) adding a RCA reaction mix to form DNA amplification products (e.g. nanoballs); and (8) sequencing the DNA nanoballs using FISSEQ.

Example 4—Probe Tethering

The example provides a protocol for tethering probes to a three-dimensional matrix. The protocol can comprise (1) permeabilizing a tissue section sample; (2) embedding the tissue section sample in a 3D matrix with 4% w/v 19:1 acrylamide:bisacrylamide with additional 0.1% propargyl acrylamide using APS/TEMED; (3) introducing a plurality of in situ hybridization (ISH) probes, such as those targeting RNA or a genomic loci, and the probes also bearing an azide modification tethering moiety and a detectable label, such as an barcode sequence domain; (4) washing the sample; (5) adding a click reaction mix comprising copper salt and sodium ascorbate, which catalyzes linkage between ISH probes and the matrix; and (6) and detecting the probes, such as by cyclic HCR as described in U.S. Patent Publication Nos. 20190218608 and 20190218608.

Example 5—Antibody Barcode Tethering

The example provides a protocol for tethering antibodies comprising barcodes to a three-dimensional matrix. The protocol can comprise (1) permeabilizing a tissue section; (2) embedding the tissue section in a 3D matrix with 4% w/v 19:1 acrylamide:bisacrylamide with additional 0.1% propargyl acrylamide using APS/TEMED; (3) delipidating the tissue section sample using a detergent solution, e.g., 4% w/v SDS in 1x borate buffer, pH 8.0; (4) introducing a plurality of DNA-barcoded primary antibodies (comprising a tethering moiety), which bind target protein analytes; (5) washing the tissue section sample; (6) adding a click reaction mix comprising copper salt and sodium ascorbate, which catalyzes linkage between antibody DNA barcode tags and matrix; (7) optionally clearing proteins using a protease reaction mix comprising 1:100 dilution of proteinase K in appropriate buffer; (8) washing the sample; and (9)

detecting the DNA barcodes, such as by FISSEQ or cyclic HCR. Some protocols for tethering antibodies comprising barcodes to a three-dimensional matrix may be combined with other protocols tethering nucleic acid probes in order to accomplish a multiomic approach whereby a combination of DNA, RNA, lipid, and protein localization data may be encoded and detected by the tethering of various combinations of probes and antibodies to a three-dimensional matrix in the same tissue section sample.

Example 6—Probe Tethering Chemistries

Figure 4:
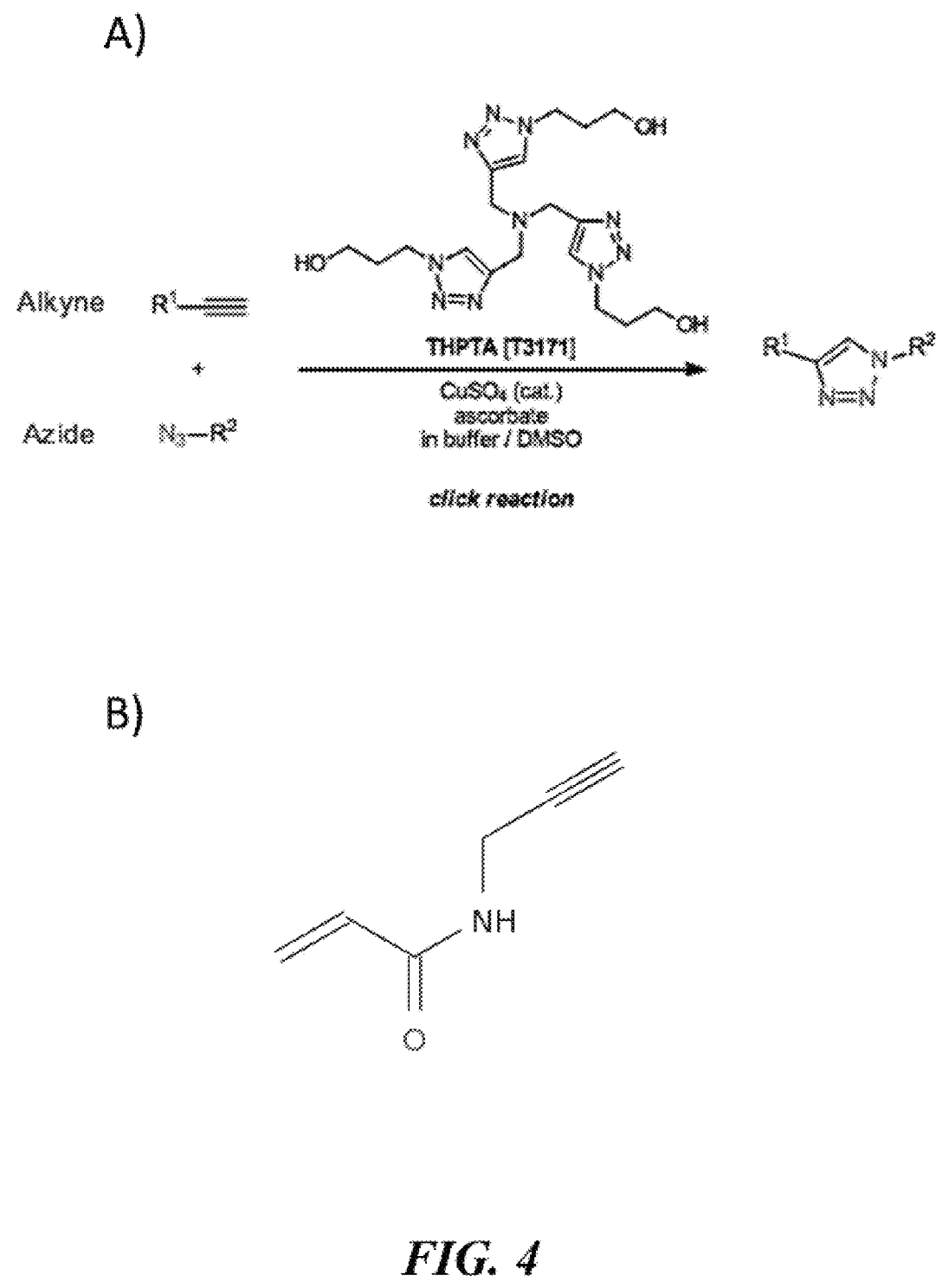
Figure 6:
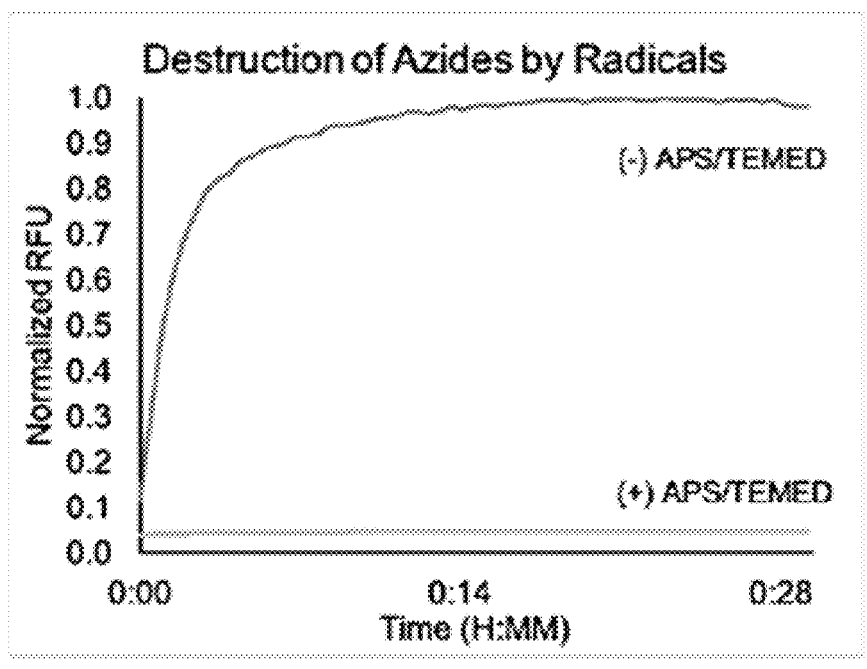
FIG. 6 (panel A) and FIG. 6 (panel B) show examples of azide functional group destruction by radicals described herein.

The example provides compositions for the use in protocols for tethering analytes, probes, and antibodies to three-dimensional matrices as described herein. In some embodiments, the method for tethering analytes, probes, and antibodies to a three-dimensional matrix utilizes click chemistry between alkyne and azide functional groups catalyzed with a copper salt and sodium ascorbate in buffer, as shown in FIG. 4 (panel A). For example, a three-dimensional matrix may be formed by crosslinking various click-reactive compounds, or click monomers, to embed click chemistry functional groups into the structure of the matrix. A click-chemistry matrix can be formed by spiking propargyl acrylamide into a gel reaction mix (FIG. 4 (panel B)). To determine the optimal amount of propargyl acrylamide to spike into the gel reaction mix, various amounts of propargyl acrylamide click monomer were spiked into gel reaction mixes as shown in FIG. 5 (panel A). FIG. 5 (panel B) is a graph depicting percent of click monomer (propargyl acrylamide) in the gel matrix and a response curve on tethering yield dependency on tethering node density, or concentration of tethering group in the gel composition. Azide functional tethering pairs may be added to the three-dimensional matrix, here a hydrogel, after matrix polymerization (FIG. 6 (panels A-B)), as azide is consumed in free radical polymerization (in the presence of APS/TEMED).

Click chemistry moieties (e.g., azide) can be utilized in various probes, nucleic acids, or antibodies for tethering to a three-dimensional matrix comprising alkyne functional groups via propargyl acrylamide polymerization. As shown in FIG. 7 (panel A), azide containing probes (e.g., azide oligo) may be hybridized to DNA nanoballs within a matrix. The nanoballs were formed in situ by phi29 rolling circle amplification (RCA) on circular templates cast into the matrix by adding RCA reagent mixes onto the gel and incubating for the amplification to occur. In some embodiments, the nanoballs contain a DNA sequence domain for binding a hybridization probe or the azide containing probe (e.g., azide oligo). Each azide containing probe (e.g., azide oligo) comprises a sequence complementary to a region on the nanoballs and other domains (e.g., an overhang region, such as for binding a detection oligo). Unbound probes were washed from the sample and a click reaction mix containing copper salt and sodium ascorbate was added to the sample catalyzing a click reaction between the azide on the probe and the alkyne in the hydrogel matrix. The sample was exposed to denaturing conditions, such as incubation and washing with 80% formamide in water, which disrupts the hybridization between the DNA nanoball and probe. Probes that are not tethered to the matrix were thereby washed from the sample. The performance of the click tethering was evaluated by comparing signals of a red fluorescent hybridization probe against the DNA sequence domain in the nanoball or a green signal from a detection oligo that binds to the overhang of the azide containing probe (FIG. 7 (panel B)). For example, a hybridization mix containing a green fluorescent probe complementary to the detection domain can be hybridized to the sample. A hybridization mix containing a red fluorescent hybridization probe complementary to the same region can be hybridized to the sample, binding to the DNA nanoballs that are not already occupied by the azide containing probe (e.g., azide oligo). Unbound fluorescent probes were washed. Imaging was performed to detect fluorescence signals from the green and red channels, thereby detecting the relative abundance of azide containing probe (e.g., azide oligo) tethered into the hydrogel matrix by the click reaction and unoccupied sequences available for binding the hybridization probe on the DNA nanoballs (e.g., predominantly by un-tethered click probes which were washed away in denaturing conditions; some minor background may be generated due to incomplete yield of hybridization reaction by click probes). FIG. 7 (panel B) shows +/− copper conditions for red and green fluorescence signals by microscopic imaging. In copper (+) conditions, green punctate signals generated by green fluorescent detection oligos binding to covalently matrix-tethered azide containing probes (e.g., azide oligos) was detected, with minimal signal from competing red fluorescence hybridization probes (e.g., "chase probes"). In copper (−) conditions, total lack of green fluorescence signal detected shows that in absence of click reaction, no azide containing probes (e.g., azide oligos) were spatially retained by the matrix after denaturing conditions.

Figure 8:
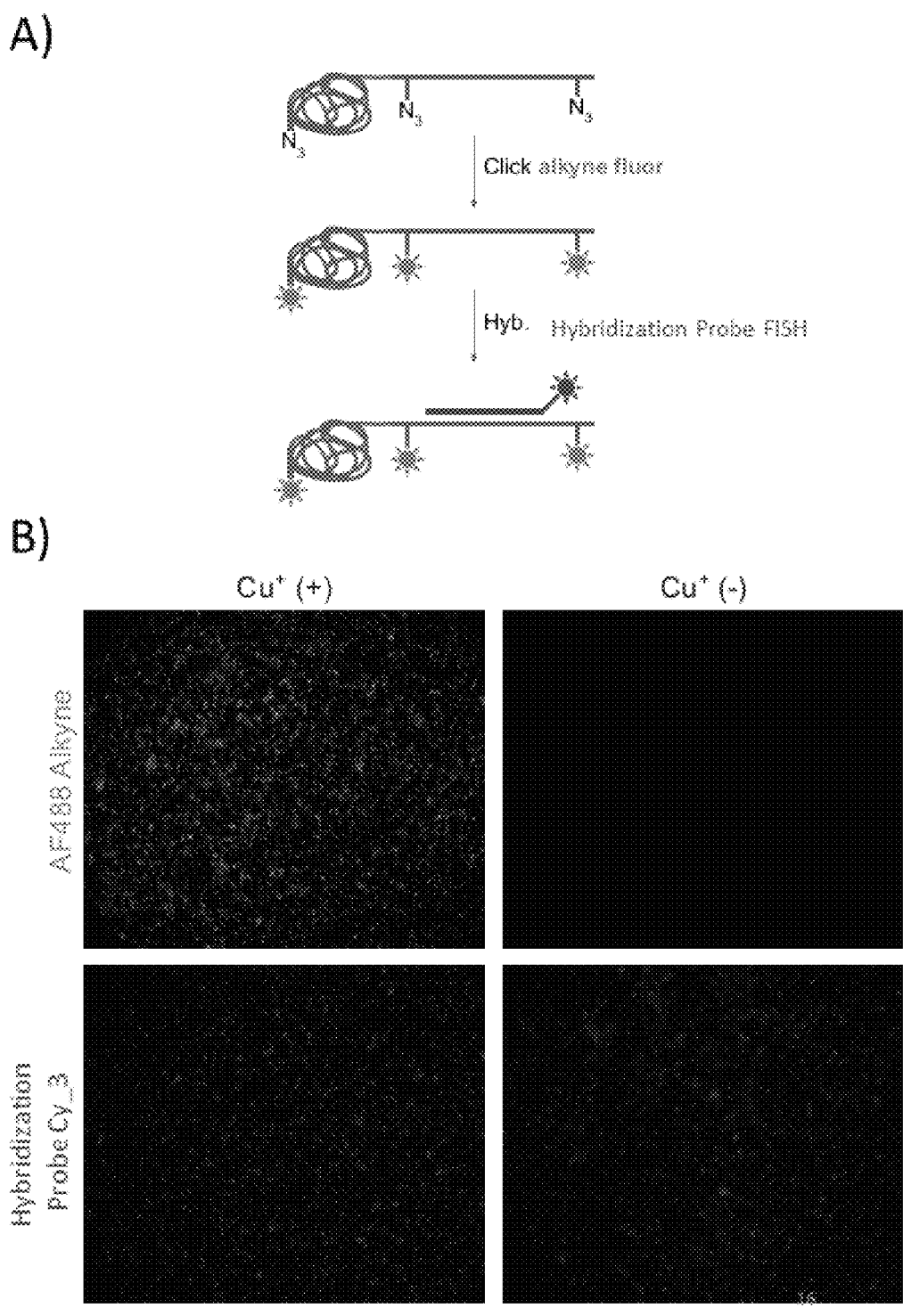
FIG. 8 (panel A) and FIG. 8 (panel B) show examples of azide probe labeling using a method described herein.

The methods described herein may also be applied to a derivative molecule formed in situ after hydrogel formation. As shown in FIG. 8 (panel A), a derivative nanoball formed by RCA, as described herein, within a hydrogel matrix lacking propargyl acrylamide (no click reactive monomers), except with the addition of azide-dUTP during RCA reaction, which is incorporated by Phi29 during RCA. A green fluorescent alkyne fluorophore was added to the sample in the presence of copper salt and sodium ascorbate, triggering a conjugation reaction of the dye to the DNA nanoball. A red fluorescent probe for hybridizing to the sequence domain on the DNA nanoball was provided, and unbound probes and dyes were washed from the sample. As shown in FIG. 8 (panel B), imaging of green and red fluorescence channels in Cu+/− conditions show that DNA nanoballs, e.g., derivative of target analyte (e.g., padlock probe to RNA or CDNA molecule) can be formed by incorporating azide functional groups reactive to click reaction conditions. It follows that azide-containing DNA-nanoballs formed within an alkyne-reactive hydrogel matrix can undergo covalent tethering to the hydrogel matrix when exposed to click reaction conditions.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing a biological sample, comprising:

(a) providing said biological sample comprising: (i) a polypeptide analyte and (ii) a nucleic acid analyte;

(b) contacting said biological sample with a tethering molecule, thereby binding said tethering molecule to said polypeptide analyte, wherein said tethering molecule comprises: (i) an antibody or fragment thereof that binds to said polypeptide analyte; (ii) a nucleic acid barcode conjugated to said antibody or fragment thereof, wherein said nucleic acid barcode identifies said antibody or fragment thereof; and (iii) a tethering moiety; and (c) contacting said nucleic acid analyte with a primer sequence, wherein said primer sequence hybridizes to a sequence of said nucleic acid analyte;

(d) extending said primer sequence hybridized to said sequence of said nucleic acid analyte to generate an extension product;

(e) contacting said tethering molecule bound to said polypeptide analyte with a matrix-forming material comprising an attachment moiety, and coupling said tethering moiety of said tethering molecule to said attachment moiety of said matrix-forming material, thereby generating a synthetic 3D matrix that is attached to said polypeptide analyte;

(f) hybridizing a probe to said extension product; and (g) subjecting said probe or derivative thereof to an amplification reaction using a modified base to generate an amplification product comprising said modified base.

2. The method of claim 1, wherein said synthetic 3D matrix comprises an additional attachment moiety.

3. The method of claim 2, wherein said attachment moiety and said additional attachment moiety are different.

4. The method of claim 2, wherein said primer sequence (i) flows through said synthetic 3D matrix and comes in contact with said nucleic acid analyte, and (ii) attaches to said nucleic acid analyte and said additional attachment moiety of said synthetic 3D matrix, thereby attaching said nucleic acid analyte to said synthetic 3D matrix.

5. The method of claim 1, further comprising contacting said biological sample with said tethering molecule and said matrix-forming material concurrently.

6. The method of claim 1, wherein said nucleic acid analyte is an RNA analyte, and wherein said extension product comprises complementary deoxyribonucleic acid (cDNA).

7. The method of claim 6, further comprising releasing said cDNA from said RNA analyte.

8. The method of claim 1, wherein said extension product is attached to said synthetic 3D matrix.

9. The method of claim 1, wherein said probe is a padlock probe or a molecular inversion probe.

10. The method of claim 1, further comprising circularizing said probe.

11. The method of claim 10, wherein said circularizing comprises ligating a 3' end and a 5' end of said probe.

12. The method of claim 1, wherein said amplification reaction is rolling circle amplification.

13. The method of claim 1, wherein said modified base is 5-azidomethyl-dUTP.

14. The method of claim 1, wherein said tethering moiety comprises an acryloyl group.

15. The method of claim 1, further comprising contacting said biological sample with said tethering molecule and said matrix-forming material sequentially.

16. The method of claim 1, further comprising subjecting said biological sample to a clearing process.

17. The method of claim 1, further comprising attaching said amplification product to said synthetic 3D matrix.

18. The method of claim 17, further comprising attaching said amplification product to said synthetic 3D matrix via a click chemistry reaction.

19. The method of claim 1, further comprising detecting said nucleic acid barcode to identify said antibody or fragment thereof, thereby identifying said polypeptide analyte in said biological sample.

20. The method of claim 1, further comprising detecting said amplification product to identify said nucleic acid analyte in said biological sample.

* * * * *